United States Patent
Dong et al.

(10) Patent No.: US 7,529,578 B2
(45) Date of Patent: *May 5, 2009

(54) MULTI CHANNEL APPROACH TO CAPTURE VERIFICATION

(75) Inventors: Yanting Dong, Shoreview, MN (US); Scott A. Meyer, Rochester, MN (US); Qingsheng Zhu, Wexford, PA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 633 days.

This patent is subject to a terminal disclaimer.

(21) Appl. No.: 11/180,937

(22) Filed: Jul. 12, 2005

(65) Prior Publication Data
US 2007/0016261 A1    Jan. 18, 2007

(51) Int. Cl.
  *A61B 5/04* (2006.01)
(52) U.S. Cl. ....................................... 600/510
(58) Field of Classification Search ................. 600/510; 607/27, 28
  See application file for complete search history.

(56) References Cited

U.S. PATENT DOCUMENTS

| | | | |
|---|---|---|---|
| 3,920,005 A | 11/1975 | Gombrich et al. | |
| 4,878,497 A | 11/1989 | Callaghan et al. | |
| 5,222,493 A | 6/1993 | Sholder | |
| 5,271,411 A | 12/1993 | Ripley et al. | |
| 5,324,310 A | 6/1994 | Greeninger et al. | |
| 5,350,410 A | 9/1994 | Kleks et al. | |
| 5,431,693 A | 7/1995 | Schroeppel | |
| 5,443,485 A | 8/1995 | Housworth et al. | |
| 5,522,860 A | 6/1996 | Molin et al. | |
| 5,626,620 A | 5/1997 | Kieval et al. | |
| 5,683,431 A | 11/1997 | Wang | |
| 5,683,434 A | 11/1997 | Archer | |
| 6,101,416 A | 8/2000 | Sloman | |
| 6,128,535 A | 10/2000 | Maarse | |
| 6,148,234 A | 11/2000 | Struble | |
| 6,163,724 A | 12/2000 | Hemming et al. | |
| 6,169,921 B1 | 1/2001 | KenKnight et al. | |
| 6,175,766 B1 | 1/2001 | Bornzin et al. | |
| 6,192,275 B1 | 2/2001 | Zhu et al. | |

(Continued)

FOREIGN PATENT DOCUMENTS

EP    0468720    1/1992

(Continued)

OTHER PUBLICATIONS

Splett et al. "Determination of Pacing Capture in Implantable Defibrillators: Benefit of Evoked Response Detection Using RV Coil to Can Vector," *PACE*, vol. 23, pp. 1646-1650, Nov. 23, 2000. Abstract only.

*Primary Examiner*—Carl H Layno
*Assistant Examiner*—Brian T Gedeon
(74) *Attorney, Agent, or Firm*—Hollingsworth & Funk, LLC

(57) ABSTRACT

Methods and systems involve classifying the cardiac response to pacing using a multi-channel approach. Multiple cardiac response signals are sensed via multiple sense channels. Each sense channel comprises a distinct combination of electrodes and sensing circuitry. The cardiac response to the pacing pulse is classified based on the morphology of the cardiac response signals. Classifying the cardiac response involves discriminating between capture, fusion, non-capture, and non-capture with intrinsic activity.

14 Claims, 16 Drawing Sheets

U.S. PATENT DOCUMENTS

| | | | |
|---|---|---|---|
| 6,221,011 | B1 | 4/2001 | Bardy |
| 6,226,551 | B1 | 5/2001 | Zhu et al. |
| 6,238,419 | B1 | 5/2001 | Lindgren |
| 6,270,457 | B1 | 8/2001 | Bardy |
| 6,275,731 | B1 | 8/2001 | Zhu et al. |
| 6,277,072 | B1 | 8/2001 | Bardy |
| 6,280,380 | B1 | 8/2001 | Bardy |
| RE37,454 | E | 11/2001 | Sutton et al. |
| 6,312,378 | B1 | 11/2001 | Bardy |
| 6,324,427 | B1 | 11/2001 | Florio |
| 6,336,903 | B1 | 1/2002 | Bardy |
| 6,345,201 | B1 | 2/2002 | Sloman et al. |
| 6,358,203 | B2 | 3/2002 | Bardy |
| 6,368,284 | B1 | 4/2002 | Bardy |
| 6,398,728 | B1 | 6/2002 | Bardy |
| 6,434,428 | B1 | 8/2002 | Sloman et al. |
| 6,440,066 | B1 | 8/2002 | Bardy |
| 6,449,503 | B1 | 9/2002 | Hsu |
| 6,456,881 | B1 * | 9/2002 | Bornzin et al. ............... 607/27 |
| 6,466,820 | B1 | 10/2002 | Juran et al. |
| 6,477,422 | B1 | 11/2002 | Splett |
| 6,493,586 | B1 | 12/2002 | Stahmann et al. |
| 6,505,071 | B1 | 1/2003 | Zhu et al. |
| 6,512,953 | B2 | 1/2003 | Florio et al. |
| 6,567,701 | B2 | 5/2003 | Vonk |
| 6,615,082 | B1 | 9/2003 | Mandell |
| 6,618,619 | B1 | 9/2003 | Florio et al. |
| 6,738,669 | B1 | 5/2004 | Sloman et al. |
| 6,768,924 | B2 | 7/2004 | Ding et al. |
| 6,950,702 | B2 | 9/2005 | Sweeney |
| 6,973,350 | B1 | 12/2005 | Levine et al. |
| 7,027,868 | B2 | 4/2006 | Rueter et al. |
| 7,319,900 | B2 | 1/2008 | Kim et al. |
| 7,330,761 | B2 * | 2/2008 | Zhang ........................ 607/28 |
| 7,337,000 | B2 * | 2/2008 | Meyer et al. .................. 607/27 |
| 2001/0049542 | A1 | 12/2001 | Florio et al. |
| 2002/0095188 | A1 | 7/2002 | Mower |
| 2002/0138111 | A1 | 9/2002 | Greenhut et al. |
| 2002/0183798 | A1 | 12/2002 | Vonk |
| 2003/0050671 | A1 | 3/2003 | Bradley |
| 2003/0083710 | A1 | 5/2003 | Ternes et al. |
| 2003/0083711 | A1 | 5/2003 | Yonce et al. |
| 2003/0204214 | A1 | 10/2003 | Ferek-Patric |
| 2004/0082975 | A1 | 4/2004 | Meyer et al. |
| 2004/0116971 | A1 | 6/2004 | Bjorling et al. |
| 2004/0116974 | A1 | 6/2004 | Obel |
| 2004/0127950 | A1 | 7/2004 | Kim et al. |
| 2004/0127951 | A1 | 7/2004 | Jarverud et al. |
| 2004/0171959 | A1 | 9/2004 | Staler et al. |
| 2004/0215277 | A1 | 10/2004 | Oosterhoff et al. |
| 2004/0243014 | A1 | 12/2004 | Lee et al. |
| 2004/0260351 | A1 | 12/2004 | Holmstrom et al. |
| 2005/0131476 | A1 | 6/2005 | Kim et al. |
| 2005/0131477 | A1 | 6/2005 | Meyer et al. |
| 2005/0131478 | A1 * | 6/2005 | Kim et al. ................... 607/27 |
| 2006/0241706 | A1 | 10/2006 | Yonce et al. |
| 2006/0247695 | A1 | 11/2006 | Stalsberg et al. |

FOREIGN PATENT DOCUMENTS

| | | |
|---|---|---|
| EP | 1291038 | 3/2003 |
| EP | 1430930 | 6/2004 |
| WO | WO2004026398 | 4/2004 |

* cited by examiner

MULTI CHANNEL APPROACH TO CAPTURE VERIFICATION

RELATED PATENT DOCUMENT

This application is related to U.S. patent application Ser. No. 11/010,973, filed Dec. 13, 2004, now U.S. Publication No. 2006/0128196, and which is incorporated herein by reference.

FIELD OF THE INVENTION

The present invention relates generally to implantable medical devices and, more particularly, to automatically classifying a cardiac response following delivery of a pacing pulse by the implantable device.

BACKGROUND OF THE INVENTION

When functioning normally, the heart produces rhythmic contractions and is capable of pumping blood throughout the body. However, due to disease or injury, the heart rhythm may become irregular resulting in diminished pumping efficiency. Arrhythmia is a general term used to describe heart rhythm irregularities arising from a variety of physical conditions and disease processes. Cardiac rhythm management systems, such as implantable pacemakers and cardiac defibrillators, have been used as an effective treatment for patients with serious arrhythmias. These systems typically comprise circuitry to sense electrical signals from the heart and a pulse generator for delivering electrical stimulation pulses to the heart. Leads extending into on, or near the patient's heart are connected to electrodes that electrically couple to the heart for sensing the heart's electrical signals and for delivering stimulation pulses to the heart in accordance with various therapies for treating the arrhythmias.

Cardiac rhythm management systems operate to stimulate the heart tissue adjacent to the electrodes to produce a contraction of the tissue. Pacemakers are cardiac rhythm management systems that deliver a series of low energy pace pulses timed to assist the heart in producing a contractile rhythm that maintains cardiac pumping efficiency. Pace pulses may be intermittent or continuous, depending on the needs of the patient. There exist a number of categories of pacemaker devices, with various modes for sensing and pacing one or more heart chambers.

When a pace pulse produces a contraction in the heart tissue, the electrical cardiac signal following the contraction is denoted the captured response (CR). The captured response may include an electrical signal, denoted the evoked response signal, associated with the heart contraction, along with a superimposed signal associated with residual post pace polarization at the electrode-tissue interface. The magnitude of the residual post pace polarization signal, or pacing artifact, may be affected by a variety of factors including lead polarization, after-potential from the pace pulse, lead impedance, patient impedance, pace pulse width, and pace pulse amplitude, for example.

A pace pulse must exceed a minimum energy value, or capture threshold, to produce a contraction. It is desirable for a pace pulse to have sufficient energy to stimulate capture of the heart without expending energy significantly in excess of the capture threshold. Thus, accurate determination of the capture threshold is required for efficient pace energy management. If the pace pulse energy is too low, the pace pulses may not reliably produce a contractile response in the heart and may result in ineffective pacing. If the pace pulse energy is too high, the patient may experience discomfort and the battery life of the device will be shorter.

Capture detection allows the cardiac rhythm management system to adjust the energy level of pace pulses to correspond to the optimum energy expenditure that reliably produces a contraction. Further, capture detection allows the cardiac rhythm management system to initiate a back-up pulse at a higher energy level whenever a pace pulse does not produce a contraction.

At times, a pacing pulse may merge with an intrinsic beat, producing a fusion beat. A fusion beat is a cardiac contraction that occurs when two cardiac depolarizations of a particular chamber, but from separate initiation sites, merge. When the heart is being paced, fusion beats exhibit various morphologies.

When the pace pulse is below the capture threshold, a loss of capture response, which only includes the residual post pace polarization, is resulted. This is referred as non-captured response. However, sometimes after a pace pulse below the capture threshold, intrinsic activity occurs early enough to appear as an evoked response after the pace. In this case, it is called non-captured intrinsic beats.

Capture may be verified by detecting if a cardiac signal following a pace pulse indicates a captured response. However, the captured response must be discerned from other possible responses. For example, fusion beats may cause false detection of capture and may lead to erroneous capture threshold values and/or erroneous automatic capture verification information. Therefore, capture determination must be properly discriminated from superimposed residual post pace polarization without capture, fusion and non-captured intrinsic beats. The present invention provides methods and systems for paced cardiac response discrimination.

SUMMARY OF THE INVENTION

The present invention involves various methods and devices for classifying cardiac responses to pacing. One embodiments of the invention involves a method of classifying a cardiac response to pacing using multiple sense channels, wherein each sense channel comprises a distinct combination of electrodes and sensing circuitry. Classification of the cardiac pacing response is performed based on morphology of cardiac response signals sensed using the multiple sense channels.

In accordance with one aspect of the invention, a first cardiac signal associated with a pacing pulse is sensed using a first sensing channel and features of the first cardiac signal are detected. A second cardiac signal associated with the pacing pulse is sensed using a second sensing channel. Features of the second cardiac signal are detected. The cardiac response to the pacing pulse is classified using at least one of the features of the first cardiac signal and the features of the second cardiac signal. Classifying the cardiac response comprises discriminating between capture, fusion, non-capture, and non-capture with intrinsic activity.

Another embodiment of the invention involves a system for determining a cardiac response to pacing. The system includes multiple sense channels configured to sense multiple cardiac response signals. Each sense channel comprises a distinct combination of sense electrodes and sensing circuitry. Cardiac response detection circuitry is coupled to the multiple sense channels. The cardiac response circuitry is configured to classify the cardiac response as one of non-capture, capture, fusion, and non-capture with intrinsic activation based on morphology of the multiple cardiac response signals.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1A:
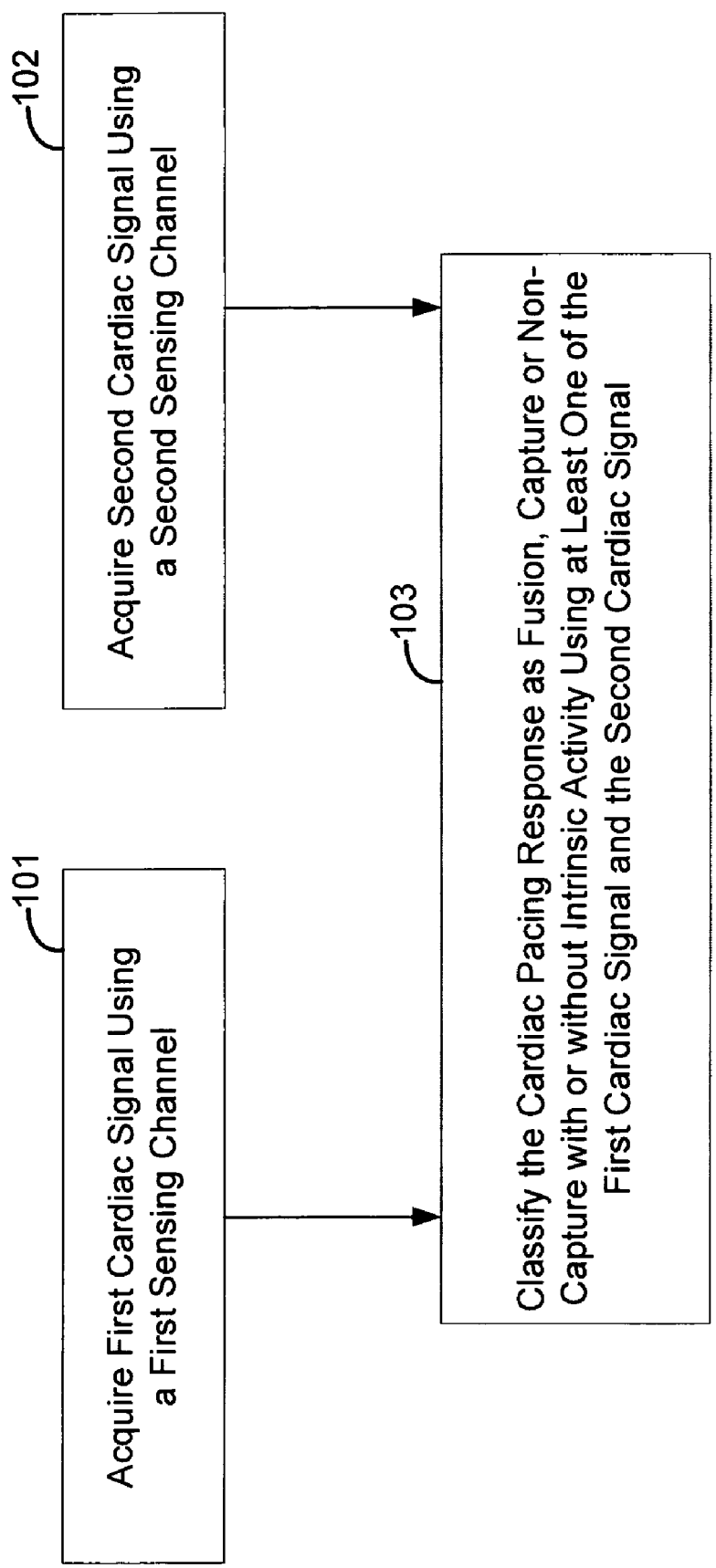
FIGS. 1A-1B are flowcharts illustrating methods for automatically classifying a cardiac response to a pacing pulse using a first and second cardiac signal in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings forming a part hereof, and in which are shown by way of illustration, various embodiments by which the invention may be practiced. It is to be understood that other embodiments may be utilized, and structural and functional changes may be made without departing from the scope of the present invention.

After delivery of a pacing pulse to a heart chamber, various cardiac responses to the pacing pulse are possible. In one scenario, the pacing pulse may generate a propagating wavefront of depolarization resulting in a contraction of the heart chamber. In this scenario, the pacing pulse is said to have captured the heart chamber. Capture of the heart chamber may occur if the pacing pulse has sufficient energy and is delivered during a non-refractory period. If the pacing pulse does not produce contraction of the chamber, the cardiac response is referred to as non-capture or loss of capture. Non-capture may occur, for example, if the pacing pulse energy is too low, and/or if the pacing pulse is delivered during a refractory period of the cardiac tissue. If, after a non-captured pace pulse, an intrinsic depolarization wavefront occurs early enough to appear as an evoked response, the beat is referred to as a non-captured intrinsic beat. In another scenario, an intrinsic depolarization wavefront may merge with a depolarization wavefront produced by the pacing pulse. The merged intrinsic and paced beats are referred to as a fusion beat.

The minimum pacing energy that produces capture is referred to as the capture threshold. It is desirable for a pace pulse to have sufficient energy to capture the heart without expending excess energy above the capture threshold. Thus, accurate determination of the capture threshold is desirable for efficient pacing. Further, fusion beats may be erroneously detected as captured beats. Discrimination between fusion and captured beats avoids erroneous detection of capture during capture threshold testing and/or during automatic beat-to-beat capture verification. The misclassification of non-captured intrinsic beat to capture or fusion beats may result in low threshold measurement during threshold testing.

Some sensing channels are more sensitive to detecting particular types of cardiac pacing response. For example, intrinsic activity may be more easily discerned and discriminated from capture based on a local sensing vector, such as tip to coil vector. A sensing vector based on a sensing vector which spans a large area over the heart, such as defibrillation coil to can vector, has better fusion classification performance. Embodiments of the invention advantageously use the sensitivity of sensing channels to particular types of pacing response for classification of the cardiac response to pacing.

Embodiments of the invention are directed to classification of the cardiac pacing response using a plurality of sensing channels. Each of the sensing channels comprises a distinct combination of electrodes and sensing circuitry. The systems and methods described herein discriminate between possible cardiac responses following pacing including non-capture, capture, fusion, and non-capture with intrinsic activity. Systems and methods according to some embodiments described herein utilize a first sensing channel to detect non-capture with or without intrinsic activity. A second sensing channel is used to differentiate between capture, fusion and non-capture.

The flowchart of FIG. 1A illustrates a method of classifying the cardiac response to a pacing pulse in accordance with embodiments of the invention. The method involves acquiring 101 a first cardiac signal associated with a pacing pulse using a first sensing channel and extracting features. A second cardiac signal associated with the pacing pulse is acquired 102 using a second sensing channel and the features are extracted. The cardiac response to the pacing pulse is determined 103 based on the features of at least one of the first cardiac signal and the second cardiac signal. Determining the cardiac pacing response may include discriminating between capture, fusion, non-capture without intrinsic activity, and non-capture with intrinsic activity, for example.

Figure 1B:
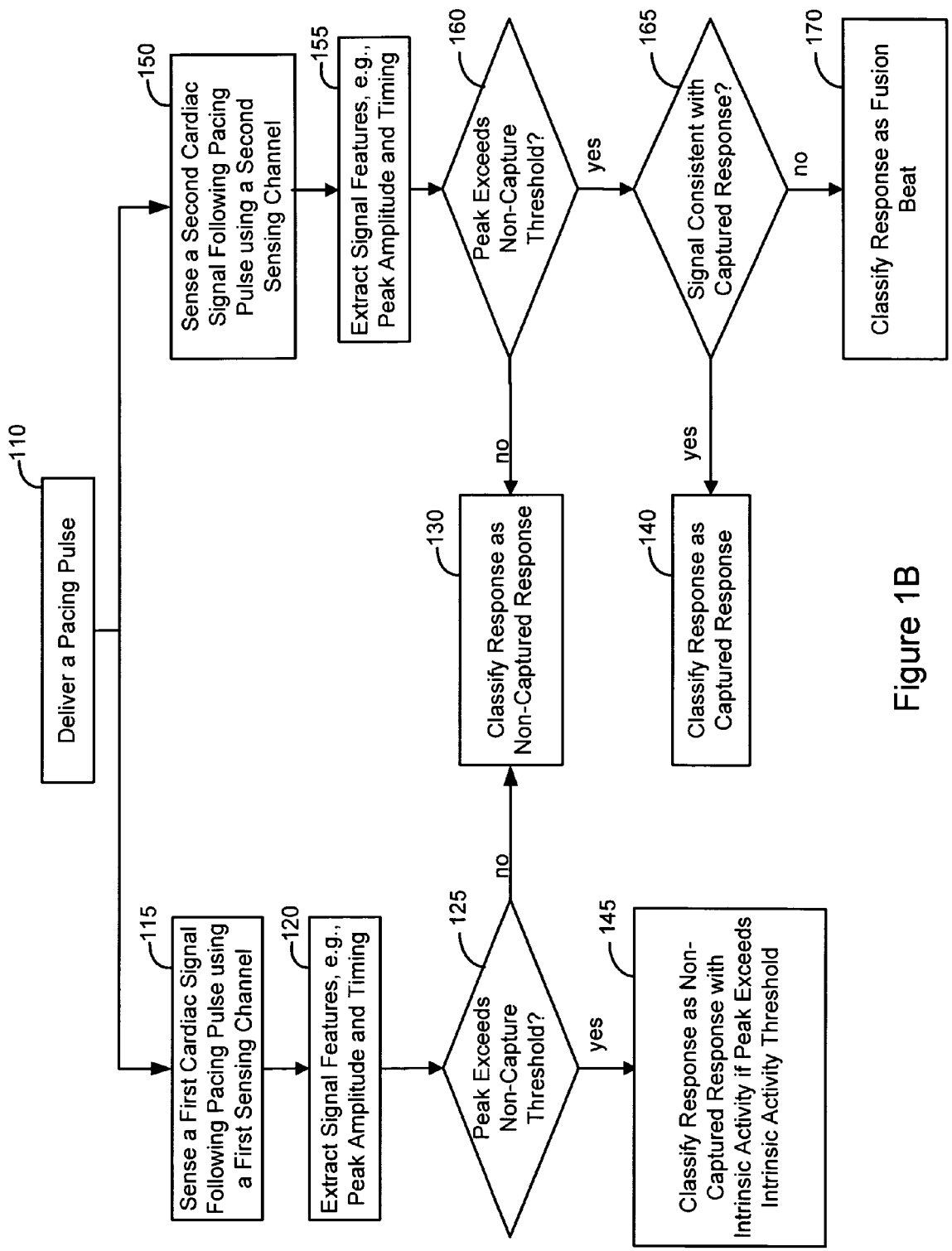

FIG. 1B illustrates a more detailed method of classifying the cardiac response to a pacing pulse in accordance with embodiments of the invention. The method involves delivering 110 a pacing pulse and sensing 115 a first cardiac signal associated with the pacing pulse using a first sensing channel. Signal features are extracted. In FIG. 1B, signal amplitude peaks are used as the features. A peak amplitude value of the signal is detected 120. If the peak of the cardiac signal does not exceed 125 a non-capture threshold, then the cardiac response to the pacing pulse is classified 130 as a non-captured response without intrinsic activity. If the peak of the cardiac signal exceeds 125 the non-capture threshold, then the system checks to determine if the signal peaks of the first signal are consistent with those of the non-capture response with intrinsic activity. Detection of intrinsic activity may be determined, for example, based on the value of one or more peaks of the cardiac signal. If the peak information acquired from the cardiac signal is consistent with intrinsic activity, then the cardiac response is classified 145 as a non-captured response with intrinsic activity.

After delivering 110 a pacing pulse, a second cardiac signal is sensed 150 using a second sensing channel. Signal features are extracted, including peak amplitude and timing. A peak amplitude of the signal is determined 155. If the peak amplitude of the cardiac signal does not exceed 160 a non-capture threshold, then the cardiac response to the pacing pulse may be classified 130 as a non-captured response without intrinsic activity. It should be noted that only one of the comparisons, 125, 160, are needed during the implementation to detect non-capture response.

If the peak amplitude of the second cardiac signal exceeds 160 the capture threshold and the signal features are consistent 165 with those of a capture response, then the cardiac response to pacing is classified 140 as a captured response. If the features are not consistent 165 with those of a capture response, then the cardiac response to pacing is classified 170 as a fusion beat.

The flowchart of FIG. 1B illustrates classification of the cardiac pacing response using two sensing channels. One sensing channel is used for detection of non-captured intrinsic activity and another sensing channel is used to discriminate between fusion and capture. Either channel can be used to detect non-capture.

FIGS. 3 through 8 illustrate detection of intrinsic activity using a first sensing vector in accordance with embodiments of the invention. FIGS. 9 through 13 illustrate detection of fusion in accordance with embodiments of the invention.

The use of a defibrillation coil, e.g., right ventricular (RV) coil, for sensing the cardiac signal following the pacing pulse enhances the discrimination ability. The enhanced sensing performance of the coil is likely associated with the relatively large surface area of the coil and better contact of the coil with the myocardium when compared to smaller electrodes. Further, due to the spatial distance between the coil and the pacing electrode, e.g. RV tip electrode, the signal at the coil is slightly delayed allowing dissipation of the pacing artifact. The time delay and the enhanced sensing ability of the coil increase the signal level present on the coil electrode following the blanking period, improving the signal detection capability. Through selecting appropriate sensing vector involving the defibrillation coil, improved performance in discriminating cardiac response can be achieved. A bipolar sensing vector, e.g. RV-tip to RV-coil, can improve the detection performance between captured and non-captured intrinsic activity. Non-captured intrinsic activity has a faster conduction because the Purkenji system is involved. Bipolar sensing is more sensitive to the conduction speed change and usually has a larger response when an intrinsic activity occurs. This property can be used to detect non-captured intrinsic activity. Unipolar sensing, eg. RV-coil to Can, is not sensitive to pacing artifact and therefore generates a more consistent capture morphology. The signal consistency can be used to enhance the classification between capture and fusion.

Therefore, in various implementations, a right ventricular signal of sufficient amplitude for detection of intrinsic activity may be sensed using a right ventricular tip/ring to right ventricular coil sensing vector; a right ventricular signal of sufficient amplitude for discrimination between capture and fusion may be sensed using right ventricular coil to Can sensing vector; a right atrial signal of sufficient amplitude for detection of intrinsic activity may be sensed using a right atrial tip/ring to superior vena-cava coil sensing vector; a right atrial signal of sufficient amplitude for discrimination between capture and fusion may be sensed using superior vena-cava coil to Can sensing vector; a left ventricular signal of sufficient amplitude for detection of intrinsic activity may be detected using a left ventricular distal/proximal electrode to left ventricular coil sensing vector; a left ventricular signal of sufficient amplitude for discrimination between capture and fusion may be sensed using left ventricular coil to Can sensing vector; a left atrial signal of sufficient amplitude for detection of intrinsic activity may be detected using a left atrial distal/proximal electrode to left atrial coil sensing vector; a left atrial signal of sufficient amplitude for discrimination between capture and fusion may be sensed using left atrial coil to Can sensing vector.

Sensing the cardiac signals using first and second sensing channels typically follows a blanking interval, which may be programmable. In one embodiment, the blanking period immediately follows the pacing pulse and has a duration of about 45 ms. This blanking interval duration supports a wide range of pacing channel coupling capacitor values, and no special coupling capacitor is required for capture determination. The duration of the blanking period may be selected, for example, to allow the pacing artifact to dissipate while retaining adequate cardiac signal strength to determine the cardiac response to the pacing pulse. After the blanking period, the system senses the cardiac signal associated with the pacing pulse and analyzes the sensed cardiac signal on first and second channels to discern the response to pacing.

Figure 2:
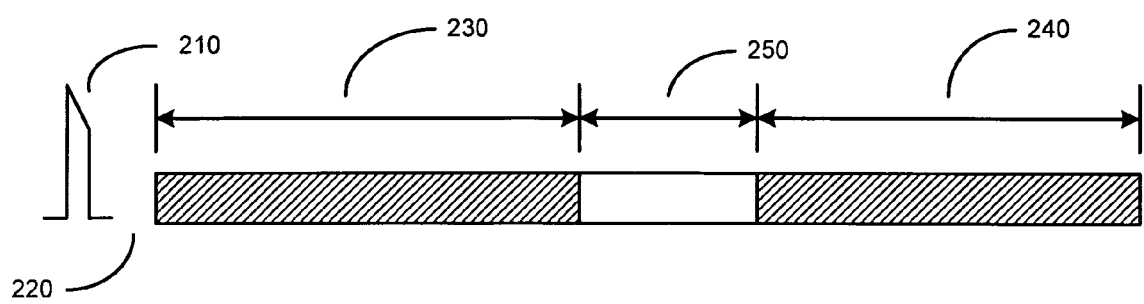
FIG. 2 illustrates time intervals that may be used in connection with the cardiac response classification methods and systems described in accordance with embodiments of the invention.

FIG. 2 illustrates time intervals that may be used in connection with the cardiac response classification methods and systems described herein. A pacing stimulation 210 is delivered to the heart, for example, to the right ventricle. The cardiac signal is blanked for a period of time 220 following pacing. Blanking may be accomplished by disconnecting the input to the sense amplifier or by otherwise rendering the sensing channel non-operational for a period of time 220. The blanking interval 220 may be programmable and may extend for example, from about 0 ms to about 45 ms following delivery of the pacing stimulation 210.

After the blanking period 220, a first classification interval 230 begins. The duration of the first classification interval may be less than about 325 ms, and may be programmable. A cardiac signal following the pacing pulse is sensed on first and second sensing channels during the first time interval 230. The system may determine if one or both of the cardiac signals sensed respectively on the first and second sensing channels attain a threshold criterion. If the cardiac signal(s) do not attain the threshold criterion, then the cardiac response to the pacing stimulation 210 may be determined to be non-capture without intrinsic activity.

If the threshold criterion is attained, then sensing may continue in one or more additional intervals, such as second classification interval 240. The use and duration of the additional classification intervals 240 may be programmable. For example, a second classification interval may have a duration of less than about 325 ms. The duration of the additional classification intervals 240 may be different from that of the first classification interval 230. Alternatively, the lengths of the first and the additional intervals 230, 240 may be the same. The cardiac response to the pacing stimulation 210 is classified based on characteristics of the cardiac signal sensed in at least one of the classification intervals 230, 240.

A delay period 250 may occur between the end of one classification interval 230 and the beginning of another classification interval 240. The length of the delay may be fixed or programmable and may be in a range of about 0 ms (no delay) to about 40 ms, for example.

In this invention, the timing for the two sensing channels may be different, including the number of classification intervals and the length of the intervals. For example, the sensing channel 1 may only have one interval while the sensing channel 2 may have 2 intervals.

Embodiments of the invention involve sensing a first signal associated with the pacing pulse using a first sensing channel for detecting non-captured intrinsic activity and sensing a second signal associated with the pacing pulse using a second sensing channel for discriminating between capture and fusion. Non-captured response without intrinsic activities can be detected by either or both of the two channels. FIGS. 3 through 8 illustrate detection of non-captured intrinsic activity using a first sensing vector in accordance with embodiments of the invention. FIGS. 9 through 14 illustrate discrimination between capture and fusion in accordance with embodiments of the invention.

Figure 3:
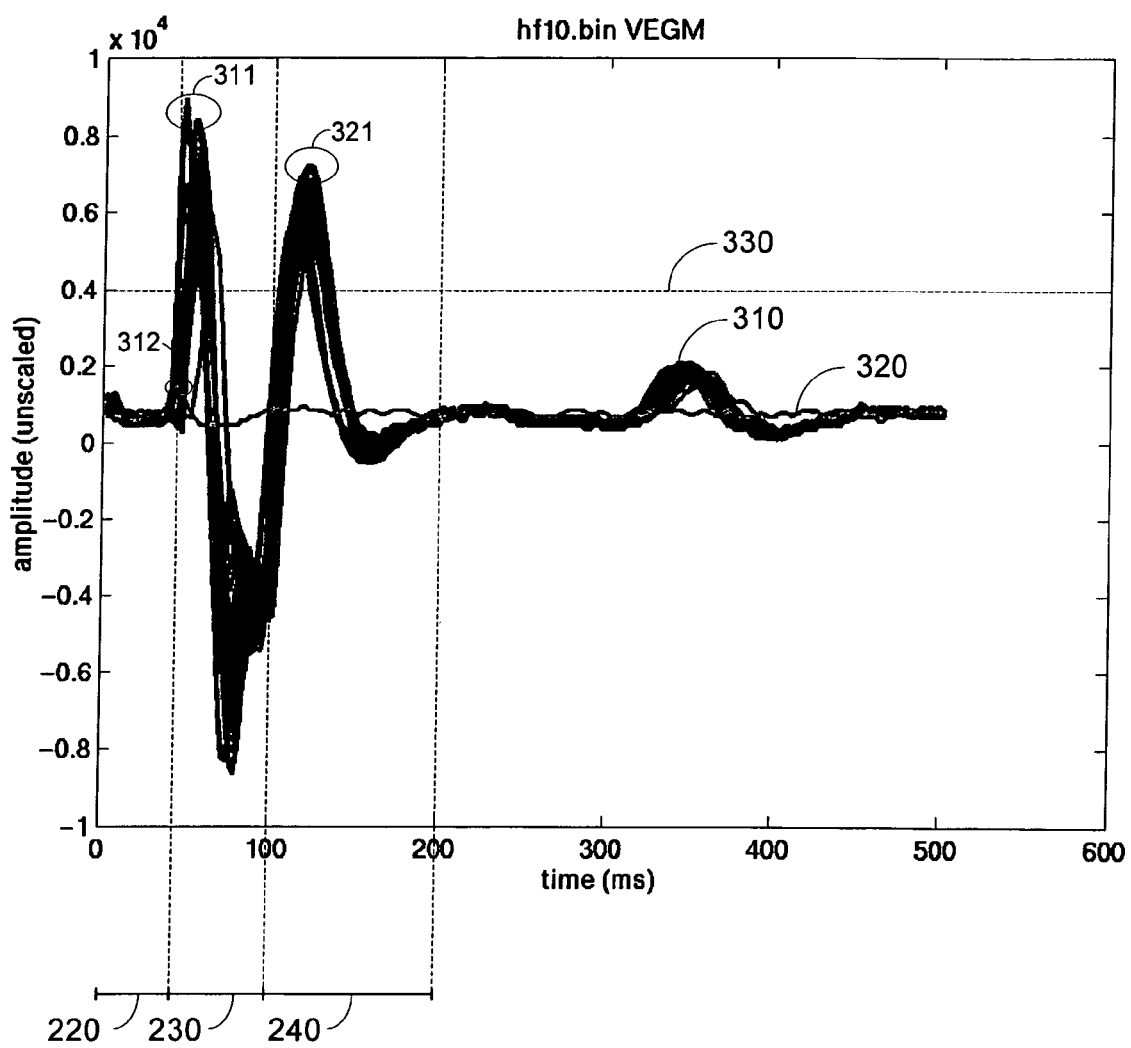
FIG. 3 graphically depicts how the morphologies of cardiac signals representative of a captured response and cardiac signals representative of a non-captured response can be utilized for cardiac response classification in accordance with embodiments of the invention.

FIG. 3 graphically illustrates the cardiac pacing response classification methods described above using the time intervals of FIG. 2. The same electrode combination may be used for pacing and sensing the cardiac signal following the pace. Alternatively, a first electrode combination may be used for pacing and a second electrode combination may be used for sensing. FIG. 3 depicts a number of cardiac signals 310 representative of a captured response superimposed on a cardiac signal 320 representative of a non-captured response. In this implementation, the system is blanked for a blanking period 220 of about 40 ms following a pacing pulse. The cardiac signal 310, 320 is sensed during a first classification interval 230. The positive peak value 311, 312 of the cardiac signal in the first classification interval 230 is detected. If the first positive peak value 312 does not attain a threshold value 330, then the cardiac response is determined to be non-capture.

Figure 4:
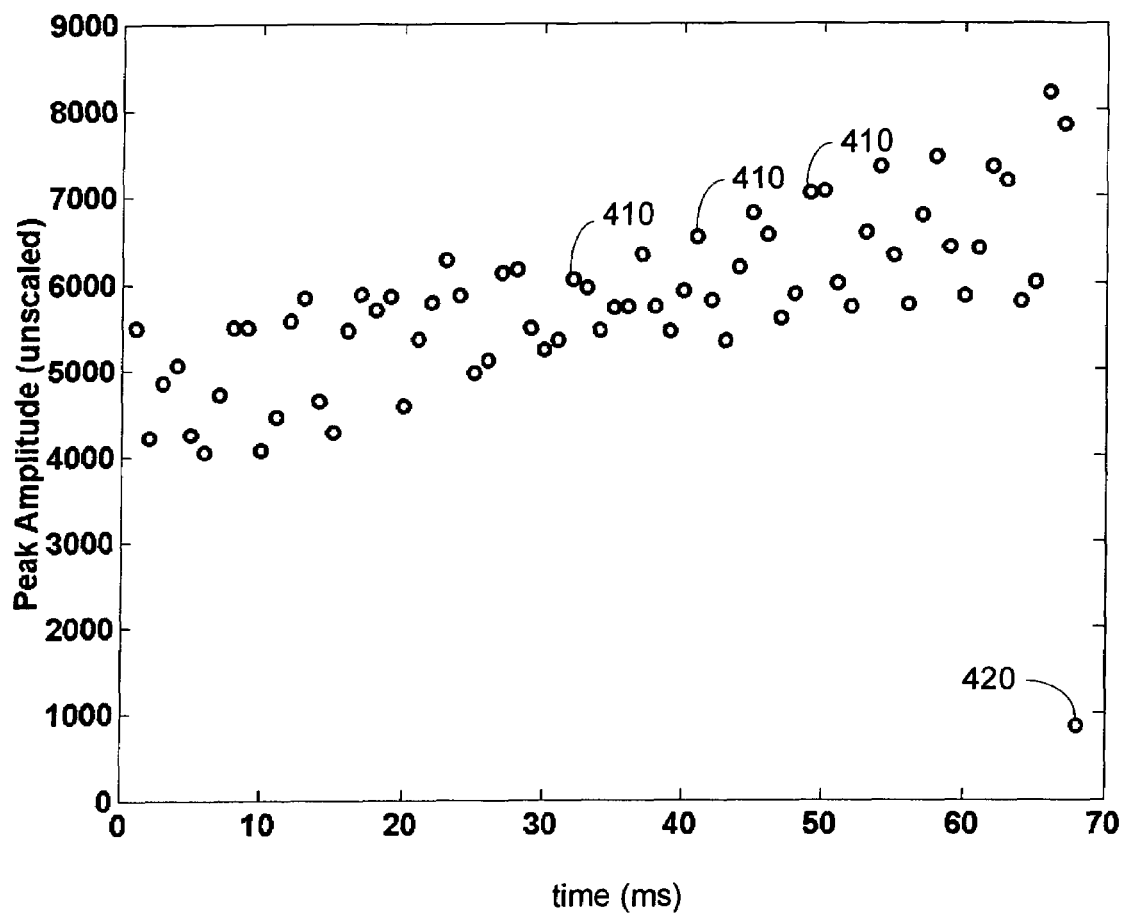
FIG. 4 is a diagram comparing peak values representative of captured responses to a peak value representative of a non-captured response, illustrating how morphological characteristics of the cardiac signals representative of captured responses and non-captured responses can be used to classify the cardiac response to pacing in accordance with embodiments of the invention.

If the first positive peak value 311, attains the threshold value 330, then the system senses for a second peak 321 of the cardiac signal 310 in the second classification interval 240. The cardiac response is determined based on at least one of the first 311 and the second 321 positive peak values. FIG. 4 illustrates the first occurring peak values 410 of a number of captured responses compared to a first occurring peak value 420 representative of a non-captured response.

Figure 5:
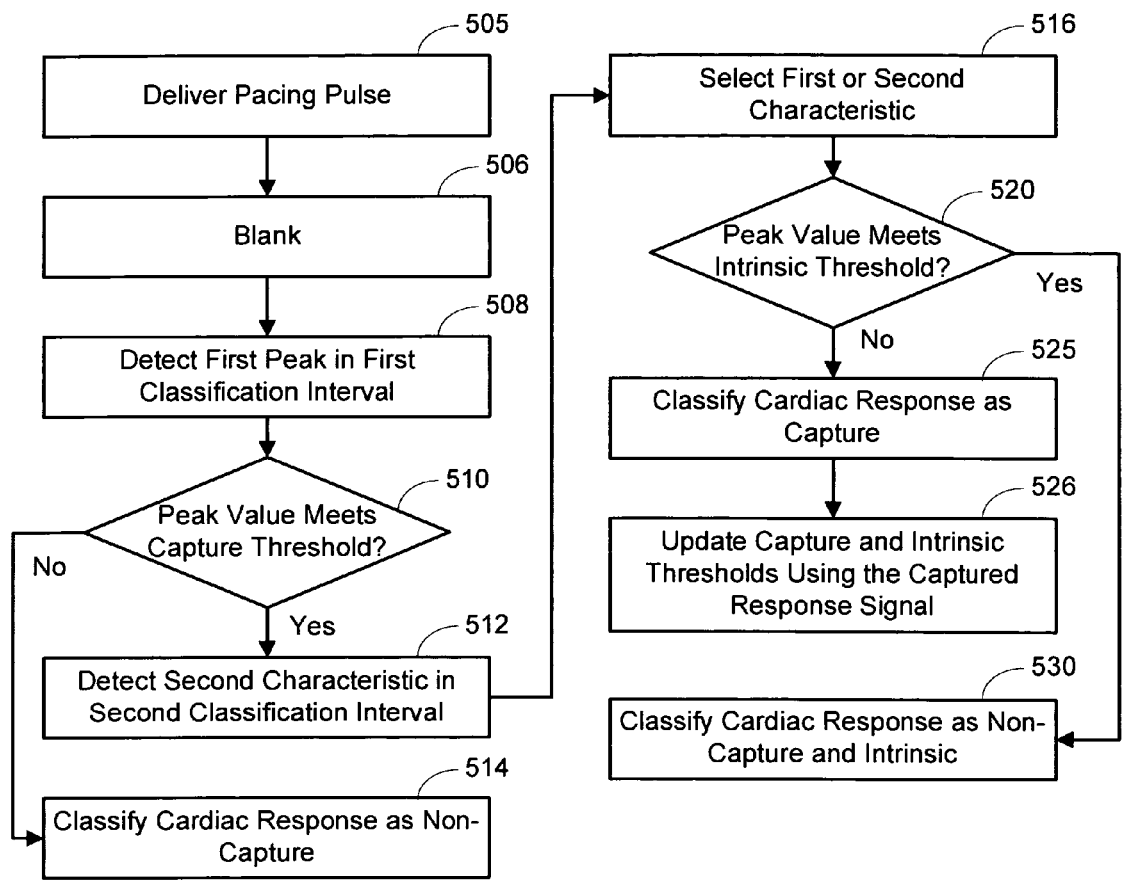
FIG. 5 is a flowchart depicting a method of determining the cardiac response to pacing using characteristic features of the cardiac electrical activity signal in the paced chamber in accordance with embodiments of the invention.

The flowchart of FIG. 5 depicts a method of determining the cardiac response to pacing using characteristic features of the cardiac electrical activity signal in the paced chamber. In this example, peak values of the cardiac signal are used to discriminate between various types of cardiac pacing responses. Other morphological characteristics may alternatively or additionally be used to determine the pacing response. For example, the morphological characteristic of the cardiac signal used to determine the cardiac pacing response may include, peak width, slope, curvature, feature timing, and/or other morphological characteristics or combinations of characteristics as previously discussed.

In accordance with this embodiment, peak values of the cardiac signal associated with a pacing pulse are used to classify the cardiac response to pacing as non-capture without intrinsic activity, capture, and non-capture with intrinsic activation. A non-captured response without intrinsic activity only includes the pace artifact, which, after a proper blanking time, has a relatively smaller peak amplitude when compared to a captured response or a non-captured response with intrinsic activity. A non-captured response with intrinsic activity produces a cardiac signal having a relatively larger peak amplitude when compared to a captured response or a non-captured response without intrinsic activation.

A method utilizing morphological characteristics of the cardiac signal following a pacing pulse to classify the cardiac response to pacing is illustrated in the flowchart of FIG. 5. A pacing pulse is delivered 505 to a cardiac chamber. For example, the pacing stimulation may be delivered to the right ventricle, the left ventricle, the right atrium, and/or the left atrium. Following a blanking interval 506, the cardiac signal associated with the pacing pulse is sensed and a cardiac signal peak is detected 508 in a first time interval following the pacing pulse.

If the cardiac signal peak detected in the first time interval does not reach 510 a capture threshold value, then the cardiac response to the pacing pulse is classified 514 as a non-captured response without intrinsic activity. If the cardiac signal peak detected in the first time interval reaches or exceeds 510 the capture threshold value, then the system detects 512 a second cardiac signal peak.

Either the first or the second detected peak value is selected 516 for comparison with an intrinsic threshold. If the selected peak value of the cardiac signal does not reach 520 the intrinsic threshold, then the cardiac response to the pacing pulse is determined 525 to be a captured response. The capture threshold and the intrinsic threshold are updated 526 using the captured cardiac signal. If the selected peak value reaches or exceeds 520 the intrinsic threshold, then the cardiac response to the pacing pulse is determined 530 to be a non-captured response with intrinsic activity.

Figure 6:
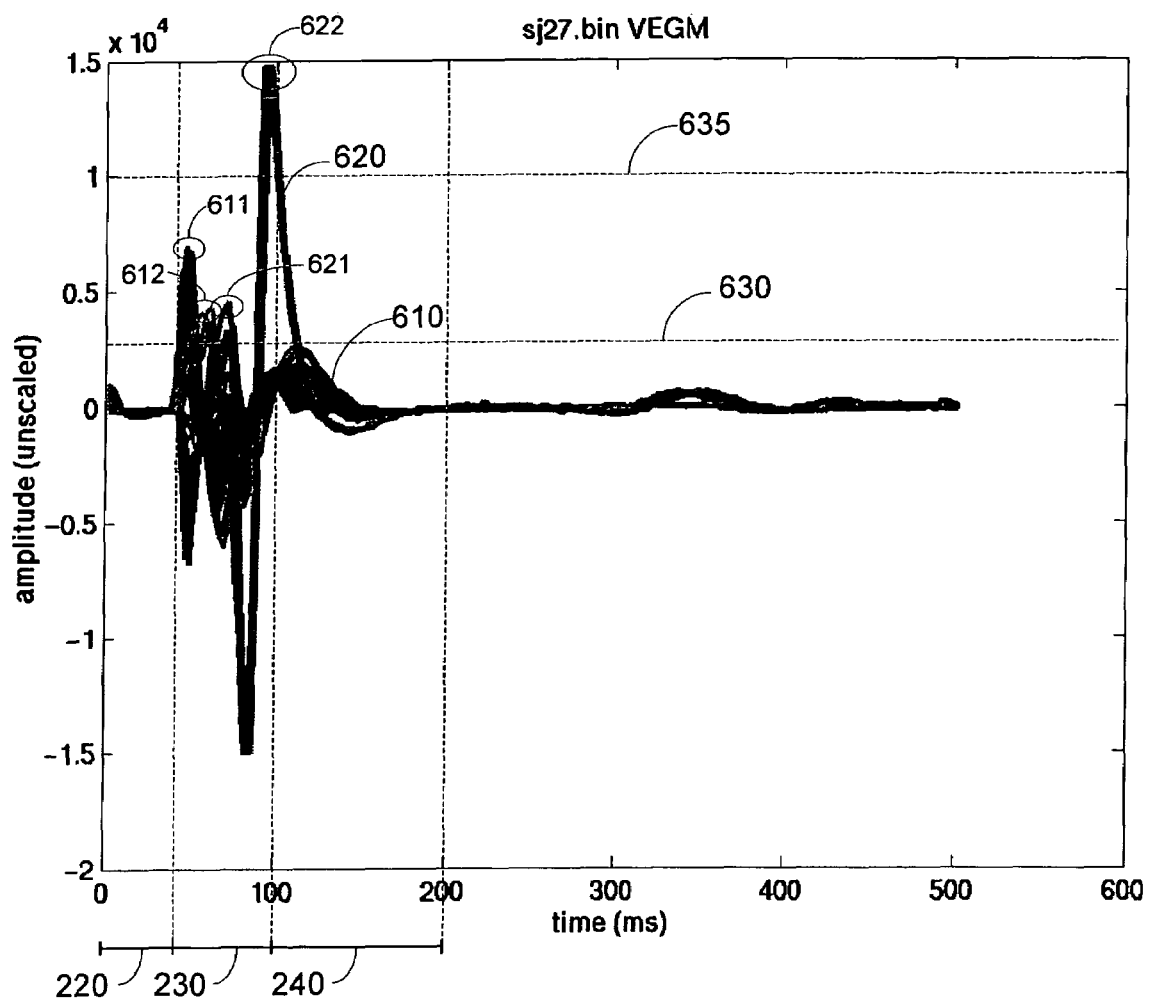
FIG. 6 graphically depicts how the morphologies of cardiac signals representative of a captured response and cardiac signals representative of a non-captured response with intrinsic activity can be utilized for cardiac response classification in accordance with embodiments of the invention.
Figure 7:
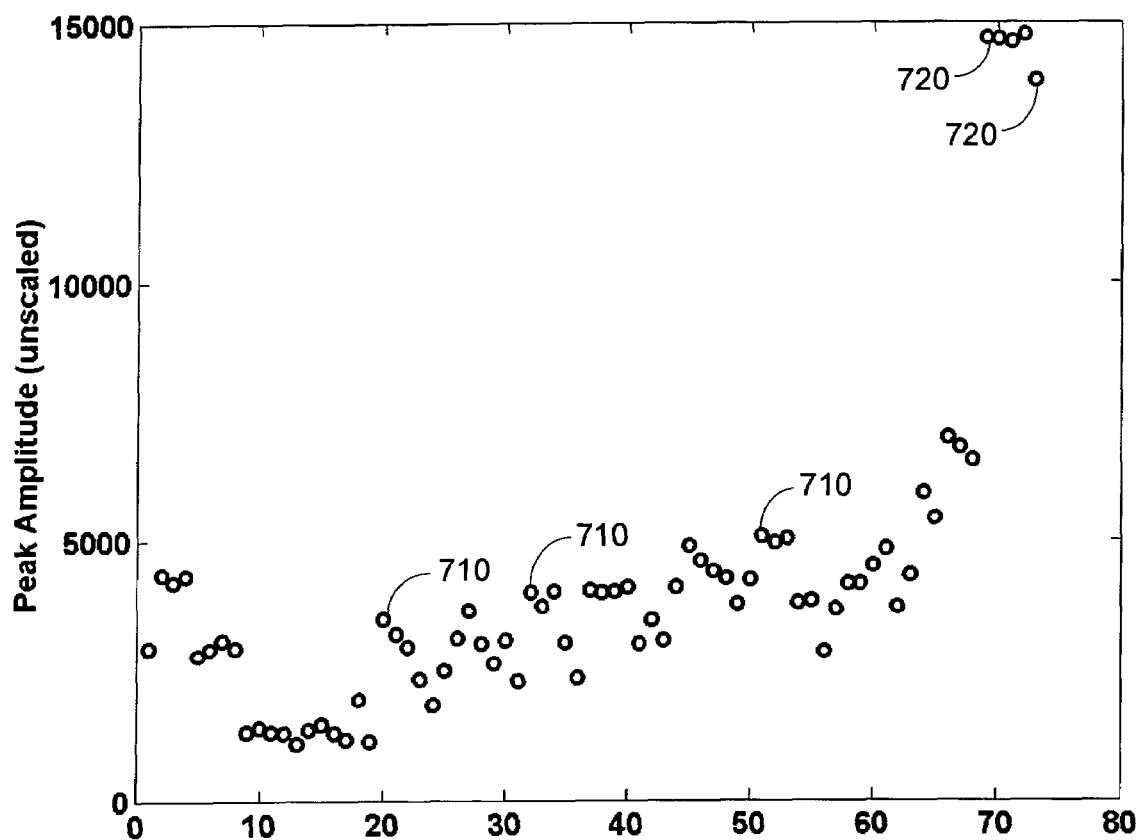
FIG. 7 is a diagram comparing peak values representative of captured responses to a peak values representative of a non-captured response with intrinsic activity, illustrating how morphological characteristics of the cardiac signals representative of captured responses and non-captured responses with intrinsic activity can be used to classify the cardiac response to pacing in accordance with embodiments of the invention.

FIGS. 6 and 7 graphically illustrate classification of the cardiac response to pacing as one of a captured response, and a non-captured response with intrinsic activity. In the example illustrated in FIGS. 6 and 7, positive peak values of the cardiac signal are used to determine the cardiac response to the pacing pulse. FIG. 7 illustrates maximum positive peak values 710 of a number of captured responses compared to maximum positive peak values 720 representative of a non-captured response with intrinsic activity. The positive peak values 720 of cardiac signals representing a non-captured response with intrinsic activity are relatively larger than the positive peak values 710 of cardiac signals representing a captured response.

FIG. 6 depicts a number of cardiac signals 610 representative of a captured response superimposed on a number of cardiac signals 620 representative of a non-captured response with intrinsic activity. The sensing system is blanked for a blanking period 220 of about 40-45 ms following a pacing pulse. First considering the captured response signals 610, the cardiac signal 610 is sensed during a first classification interval 230. The first positive peak value 611 of the cardiac signal 610 in the first classification interval 230 is determined. The first positive peak value 611, exceeds the capture threshold value 630, and the system continues to sense for the cardiac signal peak 621 in a second classification interval 240.

If the maximum of positive peaks 611 and 621 of the cardiac signal 610 does not reach the intrinsic response threshold value 635, then the cardiac response to the pacing pulse is classified as a captured response.

Next, the signals 620 representing a non-captured response with intrinsic activity are considered. The first positive peak value 612 is detected in the first classification interval 230. The first positive peak value 612 is determined to be larger than the captured response threshold 630, and the system continues to sense for the cardiac signal positive peak 622 in the second classification interval 240. The maximum of detected positive peaks 612 and 622 exceed the intrinsic response threshold 635 and the cardiac response to the pacing pulse is classified as a non-captured, intrinsic beat.

Figure 8:
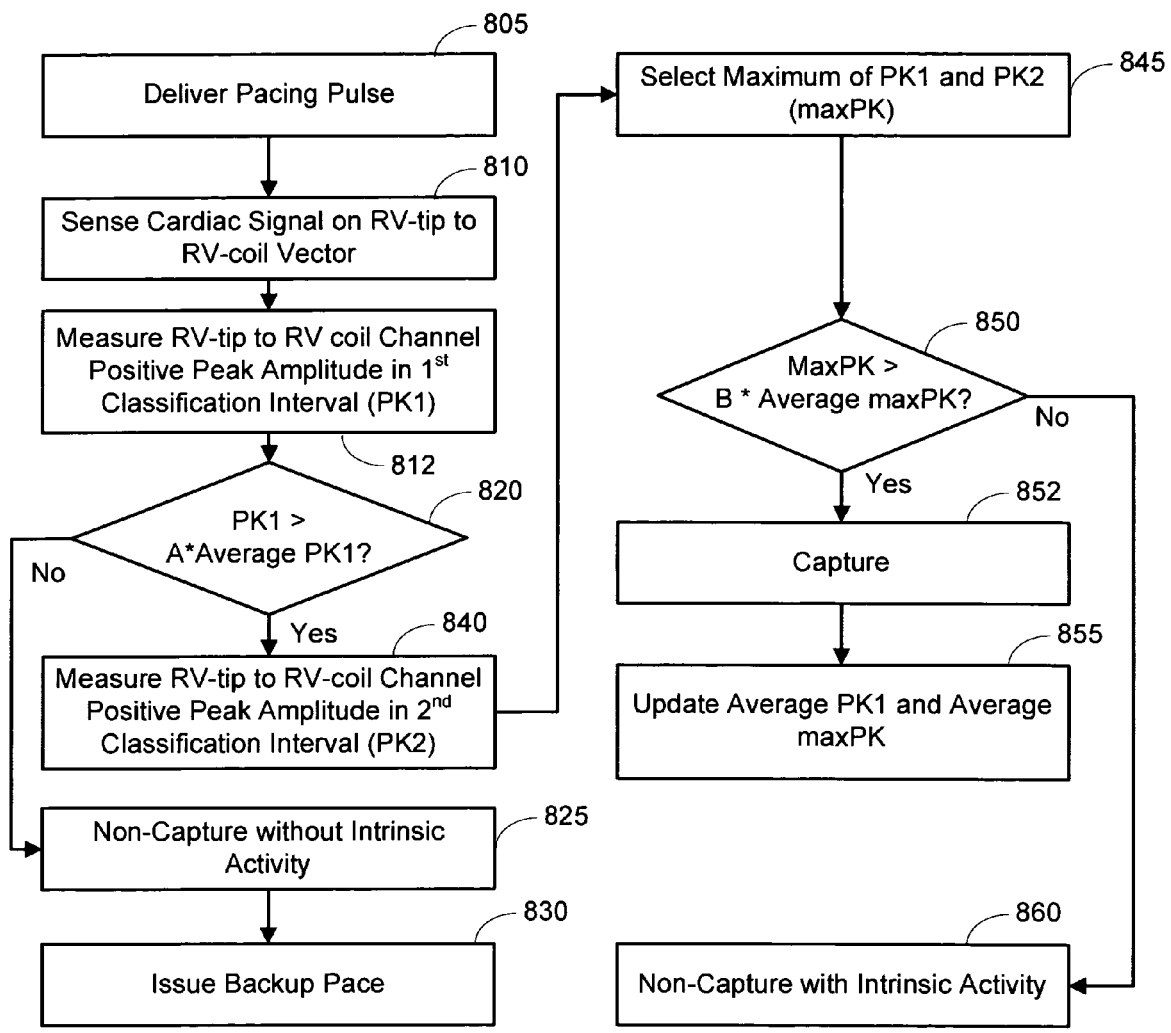
FIG. 8 is a flowchart illustrating a method of determining the cardiac response to pacing based on peak amplitudes of the cardiac signal detected in the first and/or second time intervals in accordance with embodiments of the invention.

The flowchart of FIG. 8 illustrates a method of determining the cardiac response to pacing based on peak amplitudes of the cardiac signal detected in the first and/or second time intervals, with right ventricle as an example. In this embodiment, a pacing pulse is delivered 805 to the right ventricle. Following a blanking interval, the cardiac signal following a pacing pulse is sensed 810 on the right ventricular (RV) tip to RV-coil vector. The positive peak (PK1) of the cardiac signal in the first classification time interval is determined 812 and is compared 820 to a capture threshold for discriminating between a captured response and a non-captured response. For example, the capture threshold may be a predetermined percentage of the average peak amplitude (average PK1) of captured response signals sensed on the RV-tip to RV-coil vector in the first classification interval. Thus, the capture threshold may comprise 40%, or another percentage, of the captured response average peak amplitude sensed in the first classification interval as expressed below in Equation 1:

$$\text{Capture Threshold} = A * \text{Average } PK1. \quad [1]$$

In one example, A=0.4. If the positive peak (PK1) of cardiac signal sensed on the RV-tip to RV-coil channel in the first classification interval is less than 820 the threshold criterion, then the cardiac response to pacing is classified 825 as a non-captured response without intrinsic activity. If the process is utilized in a beat to beat automatic capture verification process, a back up pace may be delivered 830.

If the peak (PK1) of the cardiac signal is greater than or equal to 820 the capture threshold, then the positive peak (PK2) of the cardiac signal in the second classification interval is determined 840. The maximum of PK1 and PK2, denoted maxPK is selected 845 and is compared 850 to the intrinsic threshold.

In the implementation illustrated in FIG. 8, the intrinsic threshold comprises a predetermined multiple of the average maximum peak amplitude of captured responses sensed in the first and second time intervals. For example, the intrinsic threshold may comprise twice the average maximum peak amplitude (average maxPK) of the captured response signals sensed in the first or second time intervals as expressed below in Equation 2:

$$\text{Intrinsic Threshold} = B * \text{Average max} PK \quad [2]$$

In one example, B=2. If the maximum of PK1 and PK2 is greater than 850 the intrinsic threshold, then the cardiac response to pacing is determined 860 to comprise a non-captured response with intrinsic activity.

If the cardiac signal is determined to be a captured response 852, the capture threshold and/or the intrinsic threshold may be updated 855. For example, capture threshold may be updated by recalculating the captured response average peak value (average PK1) in the first time interval using the current cardiac signal peak value in the first time interval as follows:

$$\text{Average } PK1_{(new)} = (1-c) * \text{Average } PK1_{(old)} + c * \text{Positive } PK1, \quad [3]$$

where Average $PK1_{(new)}$ is the updated average peak value sensed in the first time interval, Average $PK1_{(old)}$ is the previous average peak value sensed in the first time interval, Positive PK1 is the positive peak value of the current cardiac signal, and c is a constant. In one example, c=0.3.

The intrinsic threshold may be updated by recalculating the captured response average maximum positive peak value (average PK) using the current cardiac signal maximum peak value as follows:

$$\text{Average } PK_{(new)} = (1-d) * \text{Average } PK_{(old)} + d * PK, \quad [4]$$

Where Average $PK_{(new)}$ is the updated average maximum peak value of a captured response signal, Average $PK_{(old)}$ is the previous average maximum peak value, PK is the maximum peak value of the current cardiac signal, and d is a constant. In one example, d=0.3.

In FIGS. 5 and 8, if only detection of non-captured intrinsic activity is desired, one time interval is needed to compare the peak amplitude with the intrinsic threshold. If the peak amplitude is greater than the captured response, it is declared as non-captured intrinsic activity.

FIGS. 3-8 illustrate processes for detecting non-capture with or without intrinsic activity in accordance with embodiments of the invention. Such processes involve sensing the cardiac signal following a pacing pulse using a first sensing channel. For right ventricular pacing and sensing, for example, the first sensing channel may comprise the right ventricular sensing channel utilizing an RV-tip to RV-coil sensing vector.

Detection of fusion and/or discrimination between capture and fusion may be accomplished using a sensing channel and electrodes different from those used for the detection of intrinsic activity. For right ventricular sensing, for example, fusion detection may involve the use of a wide-band evoked response sensing amplifier and multiple defibrillation electrodes. For example, the cardiac signal following a right ventricular pace may be sensed for the purposes of fusion detection using the RV-coil to SVC-coil+can sensing vector.

Figure 9:
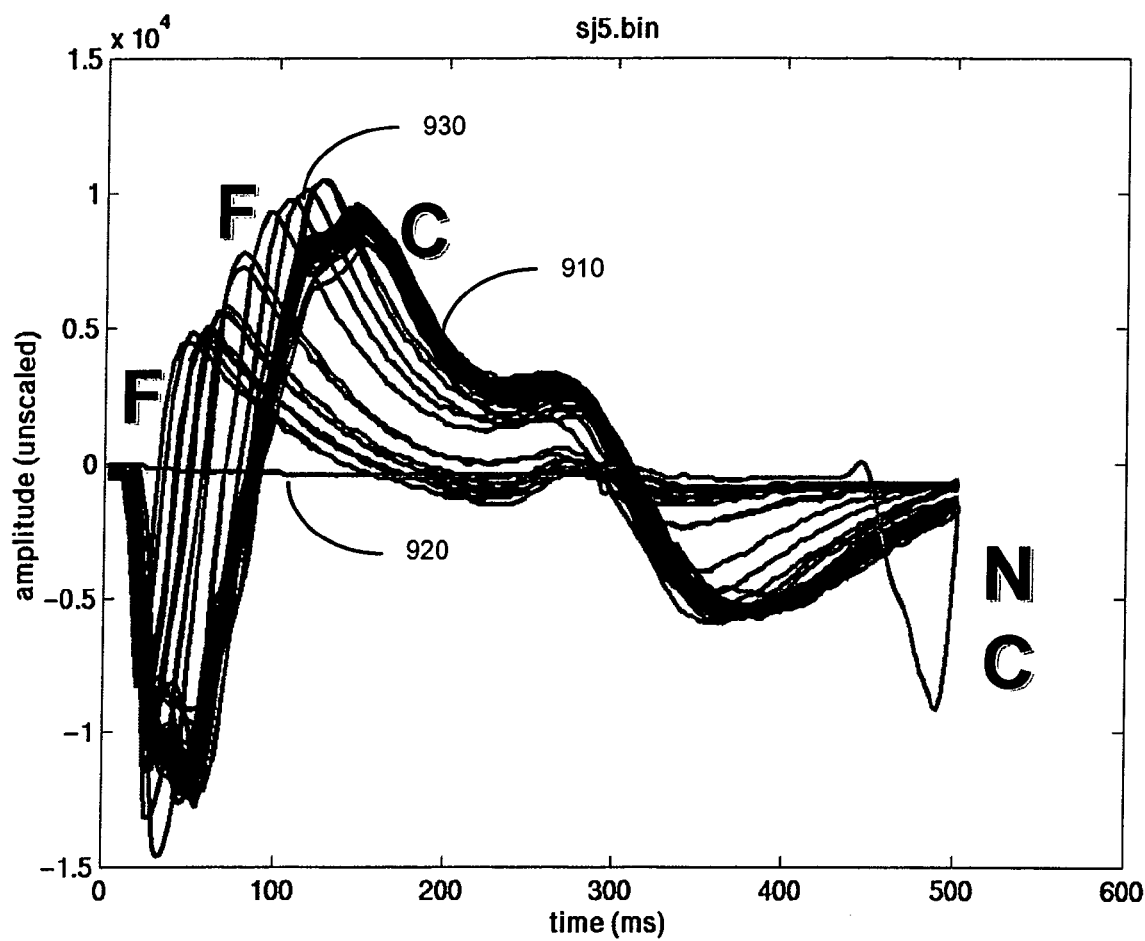
FIG. 9 illustrates superimposed graphs of captured responses, non-captured responses, and fusion/pseudofusion beats.

FIG. 9 depicts superimposed graphs of captured responses 910, non-captured responses 920, and fusion/pseudofusion beats 930. The graph of FIG. 9 represents the cardiac signal following a pacing stimulation if the pacing pulse is delivered on a RV rate channel, e.g., RV-tip to RV-coil, and the cardiac signal following pacing is sensed on a RV shock channel, e.g., RV-coil to SVC-coil or RV-coil to SVC-coil+can. The captured response exhibits a consistent morphology when detected on this vector. The stability of the captured response signal may be advantageously utilized for discrimination between fusion and capture.

Figure 10:
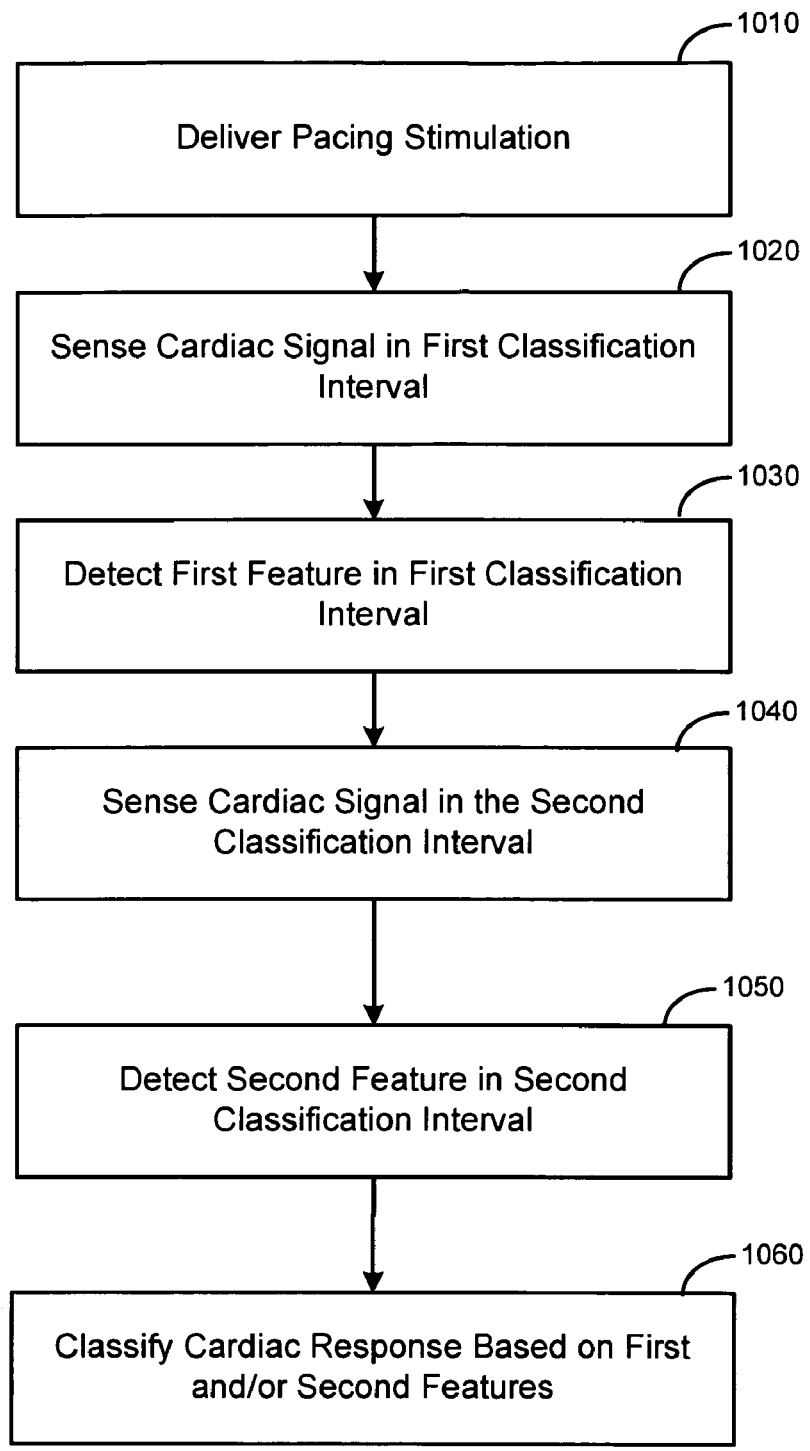
FIG. 10 is a flowchart illustrating a method of classifying a cardiac response to a pacing stimulation in accordance with embodiments of the invention.

Fusion detection may be accomplished by examining the morphology of the cardiac signal following pacing. FIG. 10 illustrates an exemplary embodiment that examines the signal morphology in multiple classification intervals. The flowchart of FIG. 10 depicts a method for discriminating between fusion and capture using two classification intervals, however, in other examples, examining the cardiac signal for indication of fusion may be accomplished using more or fewer classification intervals.

As illustrated in FIG. 10, a pacing stimulation is delivered 1010 to a heart. The pacing stimulation may be delivered to any heart chamber. For example, the pacing stimulation may be delivered to the right ventricle, the left ventricle, the right atrium, and/or the left atrium.

The cardiac signal is sensed 1020 in a first classification interval and a morphological feature, e.g., a negative peak value, of the cardiac signal is detected 1030 in the first classification interval. The cardiac signal is sensed 1040 in a second interval and a second morphological feature, e.g., a positive peak value, is detected 1050 in the second cardiac response classification interval. The cardiac response to the pacing stimulation is classified 1060 based on first and/or second sensed cardiac signal features. Although in various examples provided herein, the cardiac response classification intervals are represented as contiguous and non-overlapping, the classification intervals may be overlapping and/or may involve a delay interval defined between classification intervals.

Figure 11:
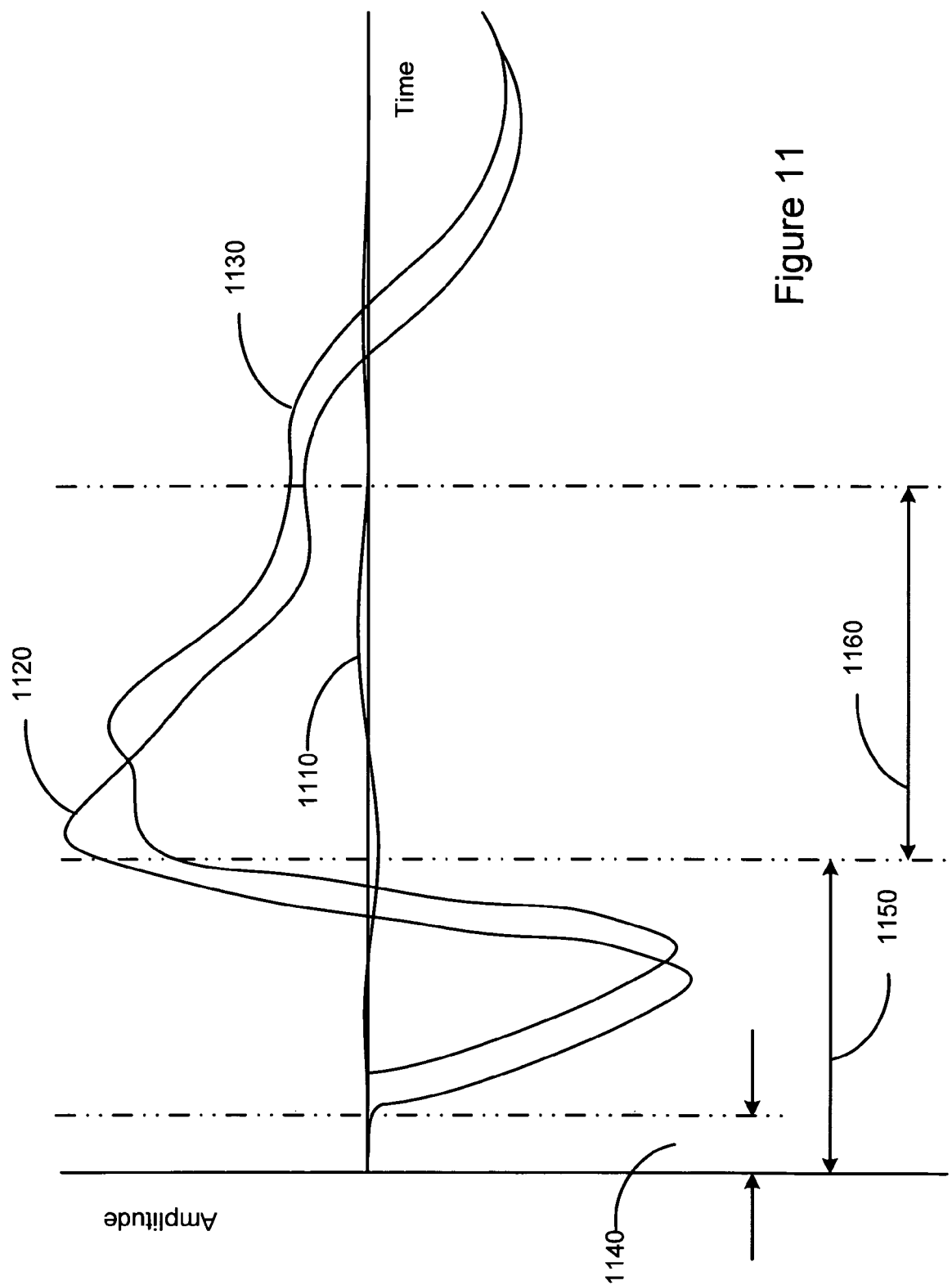
FIG. 11 illustrates cardiac signals indicative of a variety of cardiac pacing responses and their relation to the cardiac response classification intervals in accordance with embodiments of the invention.

FIG. 11 illustrates cardiac signals indicative of a variety of cardiac pacing responses and their relationships to the classification intervals previous discussed in accordance with embodiments of the invention. In the depiction of FIG. 11, cardiac signals indicative of a non-captured response 1110, a captured response 1130 and a fusion/pseudofusion beat 1120 are illustrated. A blanking period 1140 follows delivery of the pacing pulse. A first classification interval 1150 begins after the blanking interval. The system may utilize cardiac signal features detected in the first and/or the second classification 1150, 1160 intervals to discriminate between capture and fusion.

Figure 12:
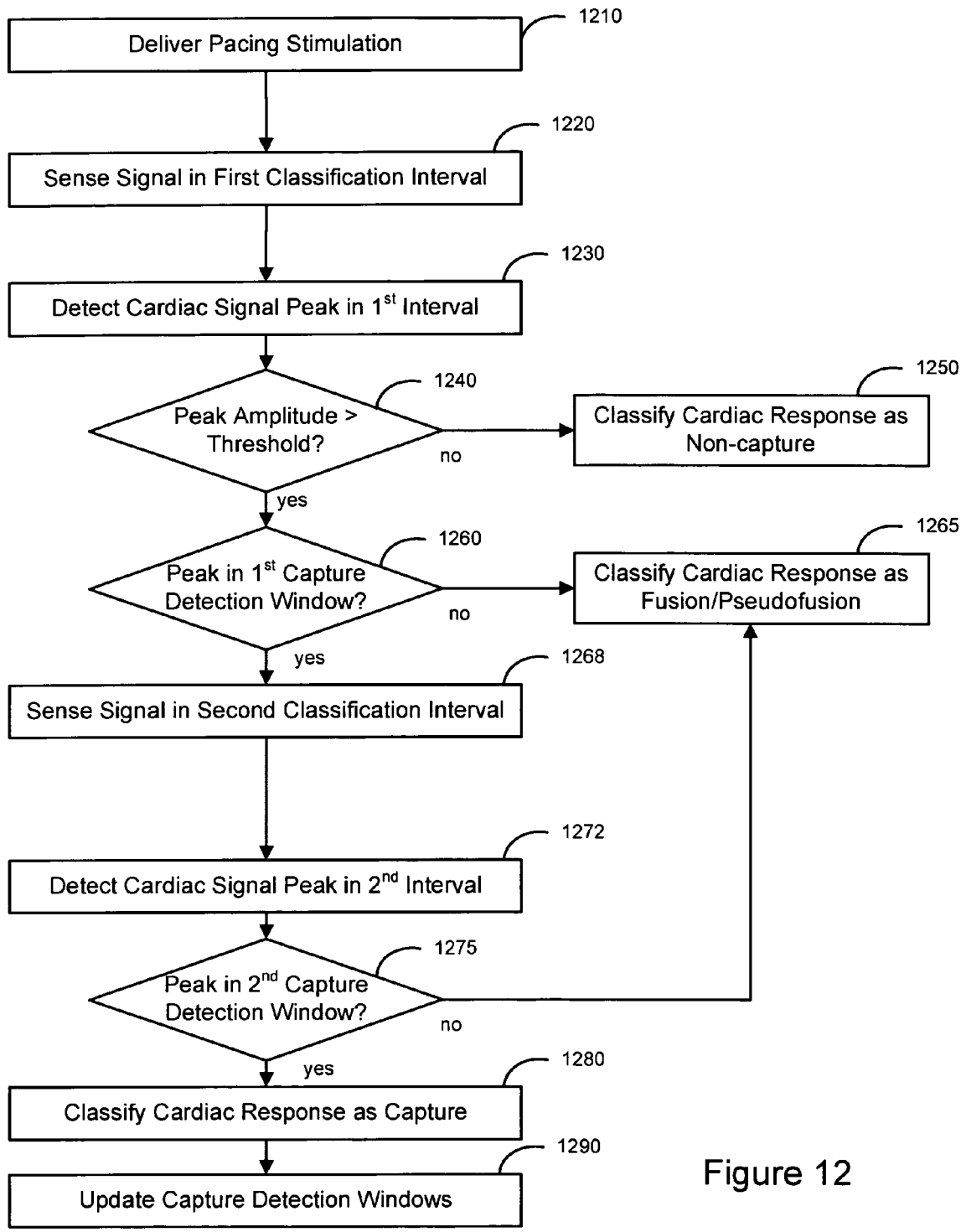
FIG. 12 is a flowchart illustrating a method of classifying the cardiac response to pacing in accordance with embodiments of the invention.

The flowchart of FIG. 12 illustrates a method of classifying the cardiac response to pacing in accordance with embodiments of the invention. The process illustrated in FIG. 12 involves first and second capture detection windows (CDWs) respectively defined in the first and the second cardiac response classification intervals. The first and second capture detection windows (CDWs) may be defined as functions of time and amplitude and are graphically illustrated in FIG. 13. The capture detection windows may be any shape, including, for example, a circle, square, rectangle, or other shape. The first capture detection window may have a shape that is different from the second capture detection window. In this example, a cardiac signal peak detected within the first capture detection window may cause the system to continue to sense the cardiac signal in a second classification interval. A peak of the cardiac signal may comprise, for example, a signal maximum value or signal minimum value that falls within the amplitude and time boundaries of a capture detection window of classification interval.

Turning now to FIG. 12, subsequent to the delivery 1210 of a pacing stimulation, the cardiac signal is sensed in a first classification interval 1220. A peak of the cardiac signal is determined 1230 in the first classification interval. If the absolute value of the peak amplitude is less or equal to 1240 a threshold value, then the cardiac response is classified 1250 as a non-captured response. If the absolute value of the peak amplitude is beyond 1240 the threshold value and is detected 1260 in the first capture detection window, then a second classification interval is established 1268. In this example, detection 1260 of a peak of the cardiac signal within the first capture detection window comprises a trigger characteristic of the cardiac signal. If the trigger characteristic is detected 1260, then the system continues to sense the cardiac signal in a second classification interval 1268.

If the peak of the cardiac signal exceeds 1240 the threshold value, but is not detected 1260 in the first capture detection window, then the cardiac response may be classified 1265 as fusion/pseudofusion.

A peak of the cardiac signal is detected 1272 in the second classification interval. If the peak does not fall 1275 within the boundaries of the second capture detection window, then the cardiac response may be classified 1265 as a fusion/pseudofusion. If the peak falls 1275 within the boundaries of the second capture detection window, then the cardiac response is classified 1280 as a captured response.

The first and/or the second capture detection windows may be updated 1290 based on the characteristics of the sensed cardiac signal. In one implementation, the location of the cardiac signal peaks in the first and the second capture detection intervals are combined with previously acquired cardiac signal peaks, for example, by averaging. The new average peak locations may be used to define the locations of subsequent capture detection windows. Various methods and systems for initializing and updating target windows including capture detection windows are described in commonly owned U.S. patent application identified by Ser. No. 10/448,260, filed May 28, 2003, now U.S. Pat. No. 7,477,932, which is incorporated herein by reference in its entirety.

Figure 13:
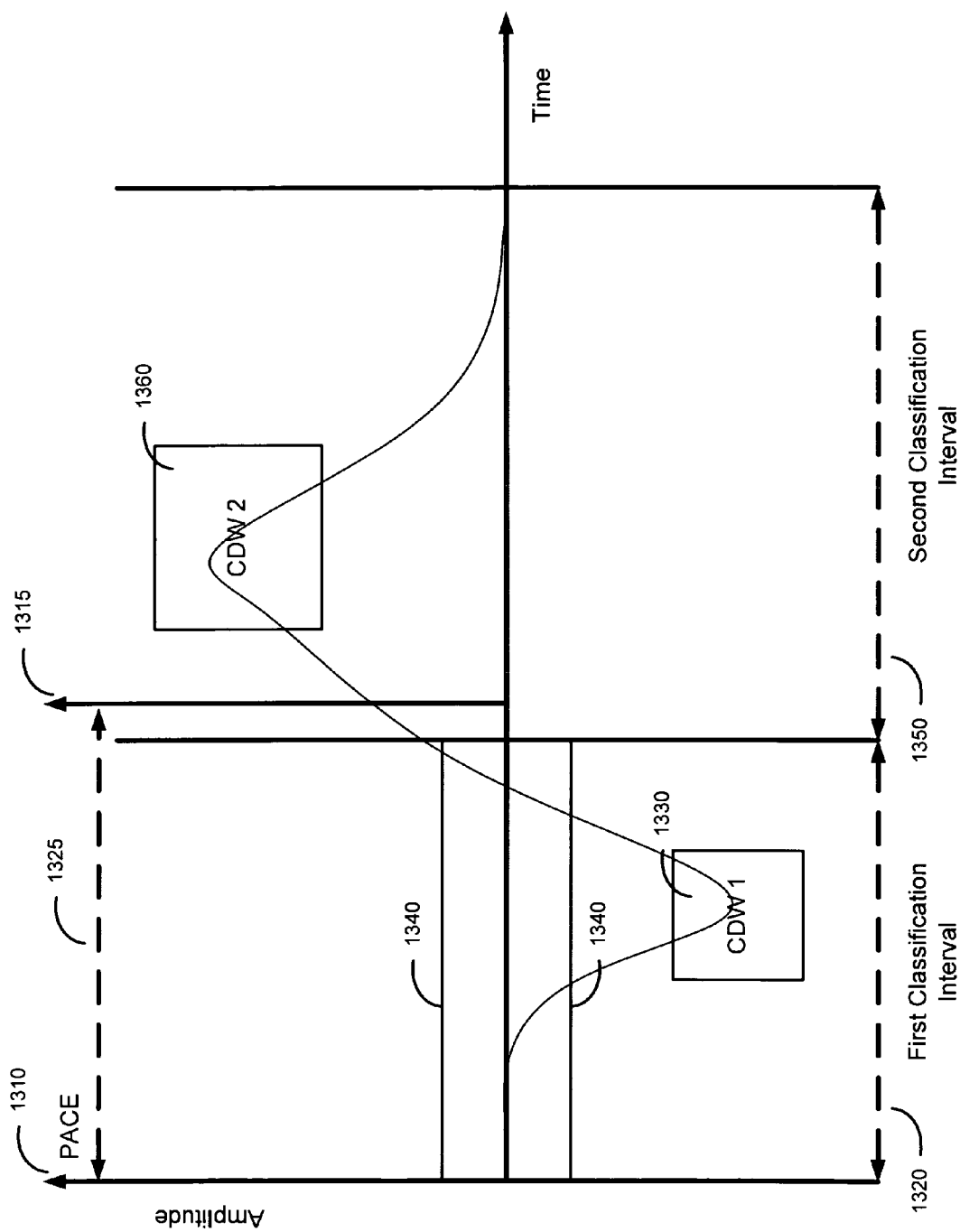
FIG. 13 is a diagram illustrating the cardiac response classification intervals and the capture detection windows described in connection with FIG. 10 and used in classifying the cardiac response to pacing in accordance with embodiments of the invention.

FIG. 13 is a diagram illustrating the classification intervals and the capture detection windows described in connection with FIGS. 10-12 and used in the discriminating between fusion and capture in accordance with embodiments of the invention. A pacing stimulation 1310 is delivered to the heart and the cardiac signal is sensed in a first classification interval 1320 timed subsequent to the delivery of the pacing stimulation 1310. A first capture detection window (CDW) 1330 is defined within the first classification interval 1320. The cardiac signal following the pacing stimulation is sensed and the peak amplitude is detected. If the peak is less than or equal to a threshold 1340, then the cardiac response may be classified as a non-captured response. If the cardiac response is classified as a non-captured response, then a back up pace 1315 may be delivered upon expiration of a back up pace interval 1325. The back up pace interval 1325 may comprise an interval of about 100 ms, for example. If a back up pace is delivered, one or more additional cardiac response classification intervals may be established to assess the effectiveness of the back up pace.

If the cardiac signal peak falls within the first capture detection window 1330, then the cardiac signal may continue to be sensed in a second classification interval 1350. The peak of the cardiac signal is detected. If the peak of the cardiac signal falls within the boundaries of the second capture detection window 1360, then the cardiac response is classified as a captured response. The cardiac response may be classified as fusion/pseudofusion if the peak of the cardiac signal falls outside the boundaries of the first capture detection window 1330 in the first classification interval 1320 and/or beyond the boundaries of the second capture detection window 1360 in the second classification interval 1350.

The classification processes of the two sensed signals may be combined to make the final classification. The beats that are detected as capture by the second sensing channel may be classified captured beats; the beats that are detected as non-captured intrinsic beats by the first sensing channel may be classified as non-captured intrinsic beats; the beats that are detected as fusion beats by the second sensing channel and are not classified as non-captured intrinsic beats may bed classified as fusion beats according to the two sensing channel classification approach.

Embodiments of the invention may employ one or more cardiac response classification intervals. Various embodiments involve discriminating between cardiac response types based on one or more characteristics of the cardiac signal detected the cardiac response classification intervals. The use of multiple classification intervals for cardiac response classification is described in commonly owned U.S. patent application Ser. No. 10/733,869, filed Dec. 11, 2003, and Ser. No. 10/734,599, filed Dec. 12, 2003, which are both incorporated herein by reference. Methods and systems for cardiac response classification involving using different pacing and sensing electrode combinations are described in commonly owned U.S. patent application Ser. No. 10/735,519, filed Dec. 12, 2003 and which is incorporated herein by reference.

By way of example, the processes of the present invention may be used to enhance capture threshold testing to determine the optimal energy for pacing. Determination of the optimal pacing energy may be implemented, for example, by an automatic capture threshold testing procedure executed by an implantable cardiac rhythm management system. Additionally, automatic capture verification may be used to monitor pacing on a beat-by-beat basis. Automatic capture verification may be used to control back up pacing when a pace pulse delivered to the heart fails to evoke a captured response (CR). These and other applications may be enhanced by employment of the systems and methods of the present invention.

Those skilled in the art will appreciate that reference to a capture threshold procedure indicates a method of determining the capture threshold in one of left atrium, right atrium, left ventricle, and right ventricle. In such a procedure, the pacemaker, automatically or upon command, initiates a search for the capture threshold of the selected heart chamber. The capture threshold comprises the lowest pacing energy that consistently captures the heart.

In one example of an automatic capture threshold procedure, the pacemaker delivers a sequence of pacing pulses to the heart and detects the cardiac responses to the pace pulses. The energy of the pacing pulses may be decreased in discrete steps until a predetermined number of loss-of-capture events occur. A capture threshold test may be performed using cardiac response classification methods of the present invention.

Other procedures for implementing capture threshold testing may be utilized. In one example, the pacing energy may be increased in discrete steps until capture is detected. In another example, the pacing energy may be adjusted according to a binomial search pattern, or other pattern.

Automatic capture threshold determination is distinguishable from automatic capture detection, a procedure that may occur on a beat-by-beat basis during pacing. Automatic capture detection verifies that a delivered pace pulse results in a captured response. When a captured response is not detected following a pace pulse, the pacemaker may deliver a back up safety pace to ensure consistent pacing. The back up pace may be delivered, for example, about 70-80 ms after the initial pace pulse. The pacemaker may adjust the pacing energy if a pacing pulse does not capture the heart. If a predetermined number of pacing pulses delivered during normal pacing do not produce a captured response, the pacemaker may initiate a capture threshold test to determine the capture threshold. Automatic capture detection and back up pacing may be implemented using the cardiac response classification processes of the present invention.

The embodiments of the present system are generally described herein as being implementable in an implantable cardiac defibrillator (ICD) that may operate in numerous pacing modes known in the art. Various types of single and multiple chamber implantable cardiac defibrillators are known in the art and may be used in connection with the cardiac response classification methods of the present invention. The methods of the present invention may be implemented in a variety of implantable or patient-external cardiac rhythm management devices, including single and multi-chamber pacemakers, defibrillators, cardioverters, rate adaptive pacemakers, bi-ventricular pacemakers, and cardiac resynchronizers, for example.

Although the present system is described in conjunction with an implantable cardiac defibrillator having a microprocessor-based architecture, it will be understood that the implantable cardiac defibrillator (or other device) may be implemented in any logic-based integrated circuit architecture, if desired.

Figure 14:
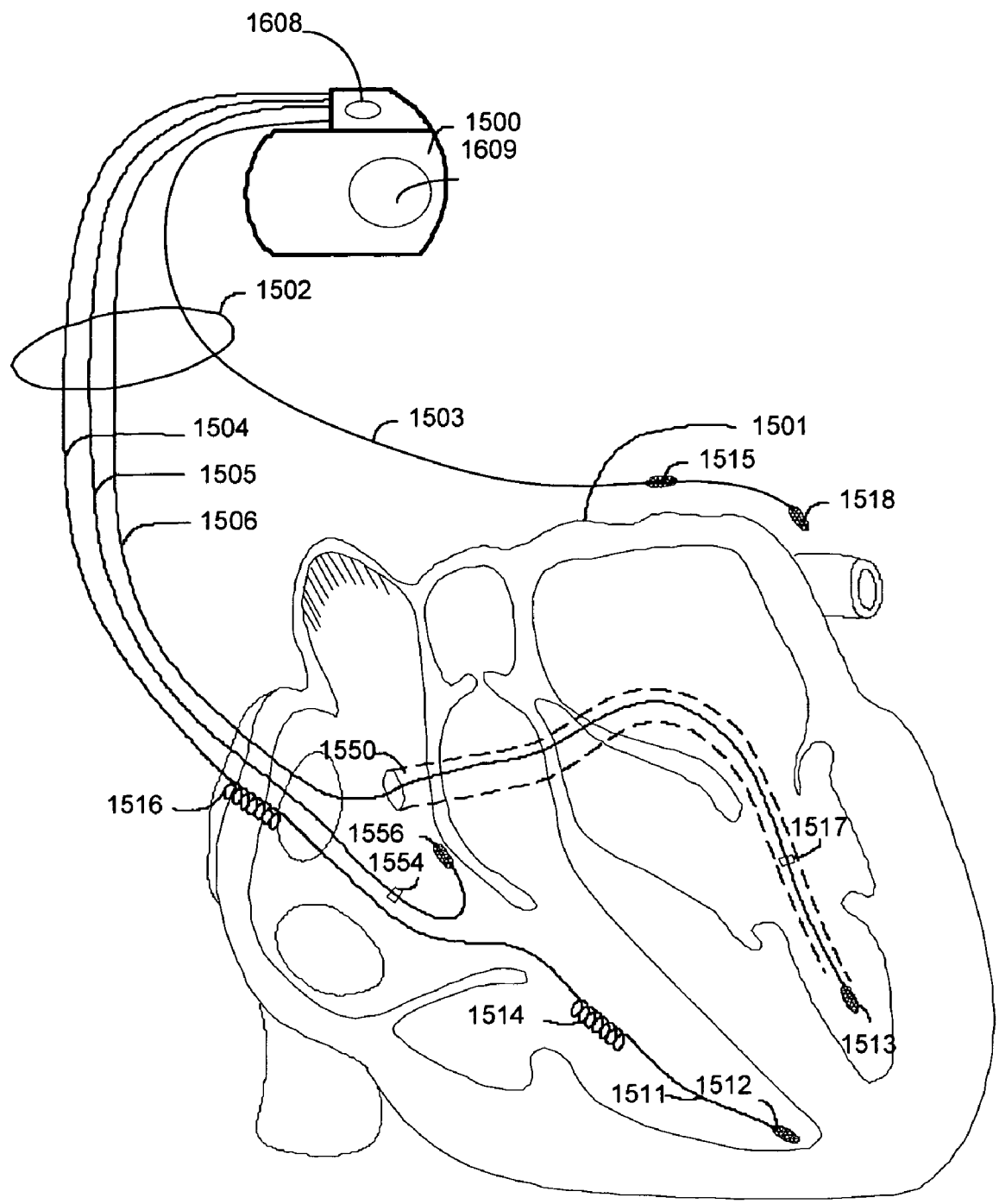
FIG. 14 is a partial view of one embodiment of an implantable medical device in accordance with embodiments of the invention.

Referring now to FIG. 14 of the drawings, there is shown a cardiac rhythm management system that may be used to implement cardiac response classification methods of the present invention. The cardiac rhythm management system in FIG. 14 includes an ICD 1500 electrically and physically coupled to a lead system 1502. The housing and/or header of the ICD 1500 may incorporate one or more electrodes 1608, 1609 used to provide electrical stimulation energy to the heart and to sense cardiac electrical activity. The ICD 1500 may utilize all or a portion of the ICD housing as a can electrode 1609. The ICD 1500 may include an indifferent electrode positioned, for example, on the header or the housing of the ICD 1500. If the ICD 1500 includes both a can electrode 1609 and an indifferent electrode 1608, the electrodes 1608, 1609 typically are electrically isolated from each other.

The lead system 1502 is used to detect cardiac electrical signals produced by the heart 1501 and to provide electrical energy to the heart 1501 under certain predetermined conditions to treat cardiac arrhythmias. The lead system 1502 may include one or more electrodes used for pacing, sensing, and/or defibrillation. In the embodiment shown in FIG. 14, the lead system 1502 includes an intracardiac right ventricular (RV) lead system 1504, an intracardiac right atrial (RA) lead system 1505, an intracardiac left ventricular (LV) lead system 1506, and an epicardiac left atrial (LA) lead system 1503. The lead system 1502 of FIG. 14 illustrates one embodiment that may be used in connection with the cardiac response classification methodologies described herein. Other leads and/or electrodes may additionally or alternatively be used.

The lead system 1502 may include intracardiac leads 1504, 1505, 1506 implanted in a human body with portions of the intracardiac leads 1504, 1505, 1506 inserted into a heart 1501. The intracardiac leads 1504, 1505, 1506 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 14, the lead system 1502 may include one or more epicardial leads 1503 having electrodes, e.g., epicardial electrodes 1515, 1518, positioned at locations outside the heart for sensing and pacing one or more heart chambers, such as the left atrium.

The right ventricular lead system 1504 illustrated in FIG. 14 includes a superior vena cava (SVC)-coil 1516, a right ventricular (RV)-coil 1514, an RV-ring electrode 1511, and an RV-tip electrode 1512. The right ventricular lead system 1504 extends through the right atrium and into the right ventricle. In particular, the RV-tip electrode 1512, RV-ring electrode 1511, and RV-coil electrode 1514 are positioned at appropriate locations within the right ventricle for sensing and delivering electrical stimulation pulses to the heart. The SVC-coil 1516 is positioned at an appropriate location within the right atrium of the heart 1501 or a major vein leading to the right atrial chamber of the heart 1501.

In one configuration, the RV-tip electrode 1512 referenced to the can electrode 1609 may be used to implement unipolar pacing and/or sensing in the right ventricle. Bipolar pacing and/or sensing in the right ventricle may be implemented using the RV-tip 1512 and RV-ring 1511 electrodes. In yet another configuration, the RV-ring 1511 electrode may optionally be omitted, and bipolar pacing and/or sensing may be accomplished using the RV-tip electrode 1512 and the RV-coil 1514, for example. The right ventricular lead system 1504 may be configured as an integrated bipolar pace/shock lead. The RV-coil 1514 and the SVC-coil 1516 are defibrillation electrodes.

The left ventricular lead 1506 includes an LV distal electrode 1513 and an LV proximal electrode 1517 located at appropriate locations in or about the left ventricle for pacing and/or sensing the left ventricle. The left ventricular lead 1506 may be guided into the right atrium of the heart via the superior vena cava. From the right atrium, the left ventricular lead 1506 may be deployed into the coronary sinus ostium, the opening of the coronary sinus 1550. The lead 1506 may be guided through the coronary sinus 1550 to a coronary vein of the left ventricle. This vein is used as an access pathway for leads to reach the surfaces of the left ventricle which are not directly accessible from the right side of the heart. Lead placement for the left ventricular lead 1506 may be achieved via subclavian vein access and a preformed guiding catheter for insertion of the LV electrodes 1513, 1517 adjacent to the left ventricle.

Unipolar pacing and/or sensing in the left ventricle may be implemented, for example, using the LV distal electrode referenced to the can electrode 1609. The LV distal electrode 1513 and the LV proximal electrode 1517 may be used together as bipolar sense and/or pace electrodes for the left ventricle. The left ventricular lead 1506 and the right ventricular lead 1504, in conjunction with the ICD 1500, may be used to provide cardiac resynchronization therapy such that the ventricles of the heart are paced substantially simultaneously, or in phased sequence, to provide enhanced cardiac pumping efficiency for patients suffering from heart failure.

The right atrial lead 1505 includes a RA-tip electrode 1556 and an RA-ring electrode 1554 positioned at appropriate locations in the right atrium for sensing and pacing the right atrium. In one configuration, the RA-tip 1556 referenced to the can electrode 1609, for example, may be used to provide unipolar pacing and/or sensing in the right atrium. In another configuration, the RA-tip electrode 1556 and the RA-ring electrode 1554 may be used to effect bipolar pacing and/or sensing.

FIG. 14 illustrates one embodiment of a left atrial lead system 1503. In this example, the left atrial lead 1503 is implemented as an epicardiac lead with LA distal 1518 and LA proximal 1515 electrodes positioned at appropriate locations outside the heart 1501 for sensing and pacing the left atrium. Unipolar pacing and/or sensing of the left atrium may be accomplished, for example, using the LA distal electrode 1518 to the can 1609 pacing vector. The LA proximal 1515 and LA distal 1518 electrodes may be used together to implement bipolar pacing and/or sensing of the left atrium.

Figure 15:
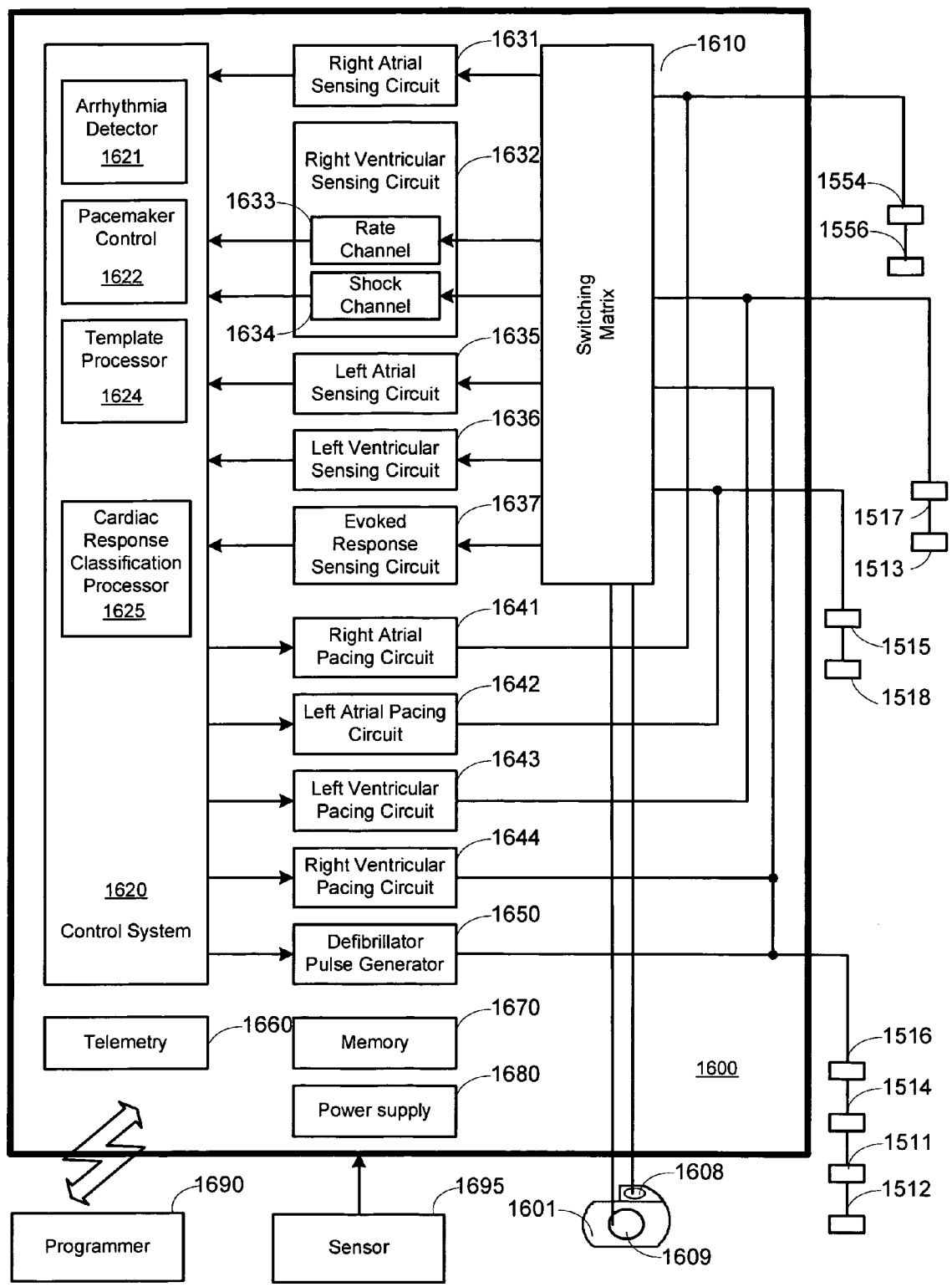
FIG. 15 is a block diagram of an implantable medical device that may be used to classify a cardiac response to pacing in accordance with embodiments of the invention.

Referring now to FIG. 15, there is shown an embodiment of a cardiac pacemaker/defibrillator 1600 suitable for implementing a cardiac response classification methodology of the present invention. FIG. 15 shows a cardiac pacemaker/defibrillator divided into functional blocks. It is understood by those skilled in the art that there exist many possible configurations in which these functional blocks can be arranged. The example depicted in FIG. 15 is one possible functional arrangement. Other arrangements are also possible. For example, more, fewer or different functional blocks may be used to describe a cardiac pacemaker/defibrillator suitable for implementing the cardiac response classification methodology of the present invention. In addition, although the cardiac pacemaker/defibrillator 1600 depicted in FIG. 15 contemplates the use of a programmable microprocessor-based logic circuit, other circuit implementations may be utilized. The cardiac pacing response classification functions described herein may be implemented using hardware, firmware, or a combination of hardware and firmware.

The configuration of one or more channels used for classifying the cardiac pacing response may be different from, or the same as, the configuration of other channels. In one example, one or more of the channels used for pacing response classification may be firmware based. In such an implementation, the sensed cardiac signals may be sampled and stored in memory. The cardiac signal features may be extracted from the stored samples. In one hardware implementation example, there may be multiple evoked response channels. In another implementation, one of the channels may comprise an evoked response channel and the other channels may comprise sensing channels for the heart chamber. Other configurations of hardware and firmware implementations of the cardiac pacing response classification system are also possible.

The cardiac pacemaker/defibrillator 1600 depicted in FIG. 15 includes circuitry for receiving cardiac signals from a heart and delivering electrical stimulation energy to the heart in the form of pacing pulses or defibrillation shocks. In one embodiment, the circuitry of the cardiac pacemaker/defibrillator 1600 is encased and hermetically sealed in a housing 1601 suitable for implanting in a human body. Power to the cardiac defibrillator 1600 is supplied by an electrochemical battery 1680. A connector block (not shown) is attached to the housing 1601 of the cardiac defibrillator 1600 to allow for the physical and electrical attachment of the lead system conductors to the circuitry of the cardiac pacemaker/defibrillator 1600.

The cardiac pacemaker/defibrillator 1600 may be a programmable microprocessor-based system, including a control system 1620 and a memory 1670. The memory 1670 may store parameters for various pacing, defibrillation, and sensing modes, along with other parameters. Further, the memory 1670 may store data indicative of cardiac signals received by other components of the cardiac pacemaker/defibrillator 1600. The memory 1670 may be used, for example, for storing historical EGM and therapy data. The historical data storage may include, for example, data obtained from long term patient monitoring used for trending or other diagnostic purposes. Historical data, as well as other information, may be transmitted to an external programmer unit 290 as needed or desired.

The control system 1620 and memory 1670 may cooperate with other components of the cardiac pacemaker/defibrillator 1600 to control the operations of the cardiac pacemaker/defibrillator 1600. The control system depicted in FIG. 15 incorporates a cardiac response classification processor 1625 for classifying cardiac responses to pacing stimulation in accordance with various embodiments of the present invention. The control system 1620 may include additional functional components including a pacemaker control circuit 1622, an arrhythmia detector 1621, along with other components for controlling the operations of the cardiac pacemaker/defibrillator 1600.

If an arrhythmia is detected by the arrhythmia detector 1621, the cardiac pacemaker/defibrillator 1600 may respond by delivering one or more of a variety of therapies to mitigate or terminate the arrhythmia. For example, the cardiac pacemaker/defibrillator may deliver anti-tachycardia pacing via one or more of the pacing circuits 1641-1644, or may delivery one or more high energy shocks to the heart via the pacemaker/defibrillator pulse generator 1650.

Telemetry circuitry 1660 may be implemented to provide communications between the cardiac pacemaker/defibrillator 1600 and an external programmer unit 1690. In one embodiment, the telemetry circuitry 1660 and the programmer unit 1690 communicate using a wire loop antenna and a radio frequency telemetric link, as is known in the art, to receive and transmit signals and data between the programmer unit 1690 and the telemetry circuitry 1660. In this manner, programming commands and other information may be transferred to the control system 1620 of the cardiac pacemaker/defibrillator 1600 from the programmer unit 1690 during and after implant. In addition, stored cardiac data pertaining to capture threshold, capture detection and/or cardiac response classification, for example, along with other data, may be transferred to the programmer unit 1690 from the cardiac pacemaker/defibrillator 1600.

In some embodiments, a sensor 1695 may be coupled to the control system 1620 of the pacemaker/defibrillator 1600. The sensor 1695 may comprise, for example, a transthoracic impedance sensor capable of sensing the patient's respiration, or an accelerometer configured to sense patient activity. The output from the sensor 1695 may be employed by the control system 1620 to adaptively control the pacing rate. Rate adaptive pacing is may be used to modify the pacing rate to accommodate changes in the patient's activity level and/or hemodynamic need.

In the embodiment of the cardiac pacemaker/defibrillator 1600 illustrated in FIG. 15, electrodes RA-tip 1556, RA-ring 1554, RV-tip 1512, RV-ring 1511, RV-coil 1514, SVC-coil 1516, LV distal electrode 1513, LV proximal electrode 1517, LA distal electrode 1518, LA proximal electrode 1515, indifferent electrode 1608, and can electrode 1609 may be coupled through a switch matrix 1610 to sensing circuits 1631-1637.

A right atrial sensing circuit 1631 serves to detect and amplify electrical signals from the right atrium of the heart. Bipolar sensing in the right atrium may be implemented, for example, by sensing voltages developed between the RA-tip 1556 and the RA-ring 1554. Unipolar sensing may be implemented, for example, by sensing voltages developed between the RA-tip 1556 and the can electrode 1609. Outputs from the right atrial sensing circuit are coupled to the control system 1620.

A right ventricular sensing circuit 1632 serves to detect and amplify electrical signals from the right ventricle of the heart. The right ventricular sensing circuit 1632 may include, for example, a right ventricular rate channel 1633 and a right ventricular shock channel 1634. Right ventricular cardiac signals sensed through use of the RV-tip 1512 electrode are right ventricular near-field signals and are denoted RV rate channel signals. A bipolar RV rate channel signal may be sensed as a voltage developed between the RV-tip 1512 and the RV-ring. Alternatively, bipolar sensing in the right ventricle may be implemented using the RV-tip electrode 1512 and the RV-coil 1514. Unipolar rate channel sensing in the right ventricle may be implemented, for example, by sensing voltages developed between the RV-tip 1512 and the can electrode 1609.

Right ventricular cardiac signals sensed through use of the defibrillation electrodes 1514, 1516 are far-field signals, also referred to as RV morphology or RV shock channel signals. More particularly, a right ventricular shock channel signal may be detected as a voltage developed between the RV-coil 1514 and the SVC-coil 1516. A right ventricular shock channel signal may also be detected as a voltage developed between the RV-coil 1514 and the can electrode 1609. In another configuration the can electrode 1609 and the SVC-coil electrode 1516 may be electrically shorted and a RV shock channel signal may be detected as the voltage developed between the RV-coil 1514 and the can electrode 1609/SVC-coil 1516 combination. Outputs from the right ventricular sensing circuit 1632 are coupled to the control system 1620.

Left atrial cardiac signals may be sensed through the use of one or more left atrial electrodes 1515, 1518, which may be configured as epicardial electrodes. A left atrial sensing circuit 1635 serves to detect and amplify electrical signals from the left atrium of the heart. Bipolar sensing and/or pacing in the left atrium may be implemented, for example, using the LA distal electrode 1518 and the LA proximal electrode 1515. Unipolar sensing and/or pacing of the left atrium may be accomplished, for example, using the LA distal electrode 118 to can vector 1609 or the LA proximal electrode 1515 to can vector 1609.

A left ventricular sensing circuit 1636 serves to detect and amplify electrical signals from the left ventricle of the heart. Bipolar sensing in the left ventricle may be implemented, for example, by sensing voltages developed between the LV distal electrode 1513 and the LV proximal electrode 1517. Unipolar sensing may be implemented, for example, by sensing voltages developed between the LV distal electrode 1513 or the LV proximal electrode 1517 to the can electrode 1609.

Optionally, an LV coil electrode (not shown) may be inserted into the patient's cardiac vasculature, e.g., the coronary sinus, adjacent the left heart. Signals detected using combinations of the LV electrodes, 1513, 1517, LV coil electrode (not shown), and/or can electrodes 1609 may be sensed and amplified by the left ventricular sensing circuitry 1636. The output of the left ventricular sensing circuit 1636 is coupled to the control system 1620.

The outputs of the switching matrix 1610 may be operated to couple selected combinations of electrodes 1511, 1512, 1513, 1514, 1515, 1516, 1517, 1518, 1556, 1554, 1608, 1609 to an evoked response sensing circuit 1637. The evoked response sensing circuit 1637 serves to sense and amplify voltages developed using various combinations of electrodes for cardiac response classification in accordance with embodiments of the invention.

Various combinations of pacing and sensing electrodes may be utilized in connection with pacing and sensing the cardiac signal following the pace pulse to classify the cardiac response to the pacing pulse. In a preferred embodiment, the RV-tip 1512 to RV-coil 1514 sensing vector, the RV-ring 1511 to RV-coil 1514 sensing vector, the LV distal electrode 1513 to LV coil electrode sensing vector, the LV proximal electrode 1517 to LV coil electrode sensing vector, the RA-tip 1556 to SVC-coil 1516 sensing vector, the RA-ring 1554 to SVC-coil 1516 sensing vector, the LA distal electrode 1518 to LA coil electrode sensing vector (not shown), or the LA proximal electrode 1515 to LA coil electrode sensing vector, is used to sense the first cardiac signal to detect non-captured intrinsic activities. The RV-coil 1514 to Can 1609 sensing vector, the LV coil to Can 1609 sensing vector, the SVC-coil 1516 to Can 1609 sensing vector, and LA coil (not shown) to Can 1609 sensing vector is used to sense the second cardiac signal to discriminate capture, fusion and non-captured activities.

Sensing the cardiac signal following a pacing pulse using the same electrode combination for both pacing and sensing may yield a sensed cardiac signal including a pacing artifact component associated with residual post pace polarization at the electrode-tissue interface. The pacing artifact component may be superimposed on a smaller signal indicative of the cardiac response to the pacing pulse, i.e., the evoked response. The presence of a large pacing artifact signal may complicate the classification of the cardiac response to pacing. By using the embodiments mentioned above which include a coil in the sensing vectors, with a suitable blanking period, the pacing artifact has dissipated substantially from the sensed cardiac signal leaving sufficient signal to determine the cardiac response to the pacing pulse. Alternatively, the pacing artifact cancellation techniques described in commonly owned U.S. patent application Ser. No. 10/335,534 now U.S. Pat. No. 7,162,301, may be utilized to reduce the effect of the pacing artifact.

The pacemaker control circuit 1622, in combination with pacing circuitry for the left atrium, right atrium, left ventricle, and right ventricle 1641, 1642, 1643, 1644, may be implemented to selectively generate and deliver pacing pulses to the heart using various electrode combinations. The pacing electrode combinations may be used to effect bipolar or unipolar pacing of the heart chambers as described above.

The cardiac response classification processor 1625 includes circuitry for determining the cardiac response to the pacing pulse. The cardiac response classification processor 1625 is primarily responsible for implementing the cardiac response classification methodologies described above. Using the above-described processes, the cardiac response classification processor 1625 may classify the cardiac response to pacing as one of a non-captured response, a captured response, a fusion response and a non-captured response with intrinsic activity as previously described. Cardiac response classification may be accomplished, for example, using multiple classification intervals defined following delivery of the pacing pulse as described in greater detail herein.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of classifying a cardiac response to a pacing pulse, comprising:
   sensing a cardiac response to a pacing pulse via multiple sense channels, each sense channel comprising a distinct combination of sense electrodes and sensing circuitry; and
   classifying the cardiac response to the pacing pulse based on morphology of cardiac response signals sensed via the multiple sense channels, wherein classifying the cardiac response comprises discriminating between capture, fusion, non-capture, and non-capture with intrinsic activity;
   wherein classifying the cardiac response to the pacing pulse comprises:
      discriminating between capture and non-capture with intrinsic activity using a first cardiac response signal sensed via a first sense channel of the multiple sense channels; and
      detecting fusion using a second cardiac response signal sensed via a second sense channel of the multiple sense channels.

2. The method of claim 1, wherein discriminating between capture and non-capture with intrinsic activity comprises determining if an amplitude of the first cardiac response signal exceeds a threshold value.

3. A method of classifying a cardiac response to a pacing pulse, comprising:
   sensing a cardiac response to a pacing pulse via multiple sense channels, each sense channel comprising a distinct combination of sense electrodes and sensing circuitry; and
   classifying the cardiac response to the pacing pulse based on morphology of cardiac response signals sensed via the multiple sense channels, wherein classifying the cardiac response comprises discriminating between capture, fusion, non-capture, and non-capture with intrinsic activity;
   wherein classifying the cardiac response to the pacing pulse comprises:
      detecting non-capture with intrinsic activity using a first cardiac response signal sensed via a first sense channel of the multiple sense channels; and
      discriminating between capture and fusion using a second cardiac response signal sensed via a second sense channel of the multiple sense channels.

4. The method of claim 3, wherein discriminating between capture and fusion using the second cardiac response signal comprises discriminating between capture and fusion based on peaks of the second cardiac signal.

5. The method of claim 4, wherein:
   discriminating between capture and fusion based on peaks of the second cardiac signal comprises:
      sensing for a first peak of the second cardiac response signal in a first capture detection window;
      sensing for a second peak of the second cardiac response signal within a second capture detection window; and
      classifying the cardiac response as capture if the first peak is detected in the first capture detection window and the second peak is detected in the second capture detection window.

6. The method of claim 5, wherein the first and the second capture detection windows have dimensions of time and amplitude.

7. The method of claim 5, further comprising classifying the cardiac response as fusion if the first peak is not detected in the first capture detection window or the second peak is not detected in the second capture detection window.

8. A system for classifying a cardiac response to a pacing pulse, comprising:
   means for sensing a cardiac response to a pacing pulse via multiple sense channels, each sense channel comprising a distinct combination of sense electrodes and sensing circuitry;
   means for classifying the cardiac response to the pacing pulse based on morphology of cardiac response signals sensed via the multiple sense channels, wherein classifying the cardiac response comprises discriminating between capture, fusion, non-capture, and non-capture with intrinsic activity;
   means for detecting non-capture with intrinsic activity using a first cardiac response signal sensed via a first sense channel of the multiple sense channels; and
   means for discriminating between capture and fusion using a second cardiac response signal sensed via a second sense channel of the multiple sense channels.

9. The system of claim 8, wherein the means for discriminating between capture and fusion using the second cardiac response signal comprises means for discriminating between capture and fusion based on peaks of the second cardiac signal.

10. The system of claim 9, wherein:
   the means for discriminating between capture and fusion based on peaks of the second cardiac signal comprises:
   means for sensing a first peak of the second cardiac response signal in a first capture detection window;
   means for sensing for a second peak of the second cardiac response signal within a second capture detection window; and
   means for classifying the cardiac response as capture if the first peak is detected in the first capture detection window and the second peak is detected in the second capture detection window.

11. The system of claim 10, wherein the first and the second capture detection windows have dimensions of time and amplitude.

12. The system of claim 10, further comprising means for classifying the cardiac response as fusion if the first peak is not detected in the first capture detection window or the second peak is not detected in the second capture detection window.

13. A system for classifying a cardiac response to a pacing pulse, comprising:
   means for sensing a cardiac response to a pacing pulse via multiple sense channels, each sense channel comprising a distinct combination of sense electrodes and sensing circuitry;
   means for classifying the cardiac response to the pacing pulse based on morphology of cardiac response signals sensed via the multiple sense channels, the classifying means comprising means for discriminating between capture, fusion, non-capture, and non-capture with intrinsic activity;
   wherein the classifying means further comprises:
      means for discriminating between capture and non-capture with intrinsic activity using a first cardiac response signal sensed via a first sense channel of the multiple sense channels; and
      means for detecting fusion using a second cardiac response signal sensed via a second sense channel of the multiple sense channels.

14. The system of claim 13, wherein the means for discriminating between capture and non-capture with intrinsic activity comprises means for determining if an amplitude of the first cardiac response signal exceeds a threshold value.

* * * * *

UNITED STATES PATENT AND TRADEMARK OFFICE
CERTIFICATE OF CORRECTION

PATENT NO. : 7,529,578 B2 Page 1 of 1
APPLICATION NO. : 11/180937
DATED : May 5, 2009
INVENTOR(S) : Dong et al.

It is certified that error appears in the above-identified patent and that said Letters Patent is hereby corrected as shown below:

In the Specification:

Col. 1, line 8: "No. 2006/0128196" should read --No. 2006/0129196--.

Signed and Sealed this

Twenty-eighth Day of July, 2009

JOHN DOLL
*Acting Director of the United States Patent and Trademark Office*